United States Patent [19]

Shaknovich

[11] Patent Number: 5,749,890
[45] Date of Patent: May 12, 1998

[54] METHOD AND SYSTEM FOR STENT PLACEMENT IN OSTIAL LESIONS

[76] Inventor: Alexander Shaknovich, 1349 Lexington Ave., Apt. 7F, New York, N.Y. 10128

[21] Appl. No.: 753,912

[22] Filed: Dec. 3, 1996

[51] Int. Cl.[6] .................................................. A61M 29/00
[52] U.S. Cl. ........................................... 606/198; 128/898
[58] Field of Search ............................... 128/898; 606/1, 606/108, 119, 191–200, 213, 151; 623/1, 11, 12; 604/96–104

[56] References Cited

U.S. PATENT DOCUMENTS 5,456,694  10/1995  Marin et al. ............................ 606/198
5,591,228  1/1997  Edoga ..................................... 606/194

Primary Examiner—Glenn K. Dawson
Attorney, Agent, or Firm—Brumbaugh, Graves, Donohue & Raymond

[57] ABSTRACT

A stent delivery assembly and method for stent placement in an ostial lesion. In particular, the stent delivery system of the invention comprises a break segment which changes configuration to facilitate localization of the target ostium.

1 Claim, 18 Drawing Sheets

METHOD AND SYSTEM FOR STENT PLACEMENT IN OSTIAL LESIONS

1. INTRODUCTION

The present invention relates to a stent delivery system to be used for stent placement in an ostial lesion. In particular, the stent delivery system of the invention comprises a stent delivery assembly having a break segment which changes configuration to facilitate localization of the target ostium.

2. BACKGROUND OF THE INVENTION

2.1. A HISTORY OF STENT DEVELOPMENT

Over the past two decades, the fields of interventional cardiology and interventional radiology have witnessed a number of paradigm shifts in the treatment of occluded (so called "stenotic") coronary arteries (among other blood vessels, various tubular conduits and similar structures). The earliest approach, still used for particular coronary applications, is by-pass surgery, which constructs a vascular detour around the occlusion.

Later, it was found that in certain patients, a much less invasive approach, which did not require thoracotomy, could be used. This technique, known as percutaneous transluminal coronary angioplasty ("PTCA"), introduces a catheter carrying a deflated balloon into a large artery in the leg or arm of a patient, threads the catheter into an occluded coronary artery, and then inflates the balloon to force open the obstruction. The balloon is then deflated, and the catheter withdrawn from the patient. PTCA has, however, two major shortcomings: first, in 3–5% of patients treated with PTCA, the treated coronary artery reoccludes within the first 24–48 hours after the procedure, despite the use of anticoagulant drugs to deter the reformation of the occlusion (called "abrupt closure"); second, in 30–50% of patients treated with PTCA, the subsequent healing process in the treated coronary artery is associated with sufficient recoil, scarring and/or proliferation of smooth muscle cells to cause re-occlusion of the artery (called "restenosis").

In hopes of preventing abrupt closure and restenosis, coronary artery stents were developed (Topol, 1994, N. Engl. J. Med. 331:539–541). Such stents are tubular devices which provide structural support for maintaining an open vessel. Recently, the placement of such stents has been found to be associated with better angiographic and clinical outcomes than PTCA (Serruys et al., 1994, N. Engl. J. Med. 331:489–495; Fischman et al., 1994, N. Engl. J. Med. 331:496–501), including a lower rate of restenosis. These benefits were achieved, however, at the price of significantly higher procedural costs related to intra- and post-procedural aspects of the stent procedure, and were associated with a significantly higher risk of periprocedural vascular complications, such as hemorrhage due to the aggressive anticoagulation regimen used after coronary stent placement. Modifications in the strategy of optimal stent placement ("deployment") have been introduced to minimize the risk of such complications.

Procedures used for stent deployment in a vessel generally involve the introduction of a stent, in a contracted condition, into a vessel and the optimal localization of the stent relative to the intended implantation or target site, followed by the expansion of the stent such that it is locked in the desired position in apposition to the vessel wall. Certain stents require an ancillary means for expansion. For example, a stent may be fitted over a collapsed angioplasty balloon, which is then introduced into the vessel and inflated, thereby expanding the stent and deploying it in the desired location. Such stents are referred to as "non-self-expanding stents". Other stents are capable of expanding when released from the contracted condition (similar to the release of a compressed spring); such stents are referred to as "self-expanding stents".

The optimal conventional strategy for implantation of non-self-expanding stents typically incorporates three distinct steps. First, where an obstruction narrows a vessel to an extent which precludes introduction of the stent delivery system, an adequate channel for passage of the balloon-stent assembly is created by inflating a balloon not carrying a stent within the stenosed region (hereafter referred to as pre-dilatation).

Second, the balloon-stent assembly is advanced into the target vessel, the collapsed stent is localized and optimally positioned relative to the intended implantation site in the stenosis, and the stent is expanded by inflating the carrier balloon, so as to achieve contact between the stent and the walls of the vessel (deployment). In order to achieve sufficient expansion of the stent along its entire length and to anchor the stent in the target vessel, the balloon used for deployment is optimally, when inflated, of the same or slightly greater diameter than the vessel adjacent to the treatment site and of the same or greater length than the stent.

Third, optimization of the axially symmetric tubular geometry of the stent and uniform circumferential contact of the stent with the walls of the vessel is achieved by inflating a balloon capable of withstanding relatively high distending pressures within the deployed stent (hereafter referred to as post-dilatation). In order to avoid damage to the target vessel adjacent to the implanted stent, the balloon used for post-dilatation is optimally of the same length or shorter than the stent. While the first and third of these three steps may occasionally be omitted, they are recommended for most stent placement applications.

For best results, the choice of balloon optimal for one of the foregoing three steps is typically not optimal for the other steps. However, when multiple balloons are used, the duration, technical difficulty and cost of the procedure increase.

2.2. SPECIAL PROBLEMS ENCOUNTERED WHEN TREATING OSTIAL LESIONS

The term "ostium" derives from the Latin os, referring to the mouth. The ostium of a vessel is located at the point of origin of the vessel. Typically, a vessel branches off from a larger parent conduit vessel. For example, the aorta gives rise to the coronary arteries; the origin of each coronary artery as it branches from the aorta is referred to as an ostium. A lesion (e.g., an atherosclerotic plaque) located at the ostium of a vessel is referred to as an "ostial lesion".

In the field of interventional cardiology, the main challenges in stenting ostial lesions in native coronary arteries, bypass grafts, renal arteries, subclavian or innominate artiers, carotid arteries and any other vessels arising from the aorta are (i) the difficulty involved in precisely localizing the ostium itself angiographically during stent delivery and implantation; (ii) the unpredictable interactions between the guiding catheter and the stent delivery system; and (iii) optimal placement of the stent covering the ostium of the target vessel without significant length of the stent protruding into the parent vessel. The guiding catheter is optimally positioned outside the ostium but in sufficient proximity to opacify the adjacent aorta and thereby localize the target ostium. However, the guiding catheter must be maintained at a sufficient distance from the ostium to avoid dislodging or damaging the stent. Maintaining proper position of the guiding catheter and stent assembly may be further complicated by forceful blood flow through the parent vessel, e.g., the aorta.

3. SUMMARY OF THE INVENTION

The present invention relates to a stent delivery system to be used in the placement of one or more stents in an ostial lesion in a patient in need of such treatment. In particular, the stent delivery system of the invention comprises a stent delivery assembly having a distally located deployment segment, wherein the deployment segment comprises a break segment which has an alterable configuration, as well as a stent-bearing segment. The break segment may be introduced into the patient in a first configuration. Then, when in proximity to the ostial lesion, the configuration of the break segment may be altered to assume a second, expanded, configuration which may be lodged against the wall of the parent conduit vessel, thereby localizing the ostium of the target vessel containing the lesion and ensuring that the stent(s) is(are) in the proper position for deployment. The dimension of the break segment in its expanded configuration orthogonal to the long axis of the target vessel is greater than the diameter of the ostium of the target vessel. One or more stents mounted, in a contracted configuration, on the deployment segment, may then be deployed by expanding the deployment segment. The configuration of the break segment may then be reversed to assume the first (unexpanded) configuration, and the entire assembly may be withdrawn from the patient.

The ostial stent delivery system of the invention may be used to avoid the complications associated with conventional methods of ostial stent placement by enabling accurate localization of the target ostium while protecting the stent from being damaged or dislodged by, for example, a guiding catheter.

4. BRIEF DESCRIPTION OF THE FIGURES

FIG. 1. Deployment segment of ostial stent delivery system in (A) deactivated, and (b) activated, configuration.

FIG. 2. Deployment segment of ostial shuttle showing forward break segment in (A) deactivated, and (B) activated, configuration.

FIG. 3. Deployment segment of ostial shuttle wherein mechanism of activation of forward break segment is a balloon in (A) deactivated, and (b) activated, configuration.

FIG. 4. Deployment segment of ostial shuttle wherein mechanism of activation of forward break segment is a nitinol wire in (A) deactivated, and (B) activated, configuration.

FIG. 5. Deployment segment of ostial shuttle wherein mechanism of activation of forward break segment is a pair of articulated wires in (A) deactivated, and (B) activated, configuration.

FIG. 6. Introduction of ostial shuttle, via a guiding catheter passed over a guide wire, into the proximity of the target ostial lesion.

FIG. 7. Pre-dilatation of ostial lesion by inflation of a balloon comprised in a catheter passed over the guide wire.

FIG. 8. Advancement of the balloon distally in the target vessel, past the ostial lesion.

FIG. 9. Advancement of the ostial shuttle, via the guiding catheter, over the shaft of the balloon catheter, into the target vessel.

FIG. 10. Withdrawal of the guiding catheter out of the target vessel and into the aorta.

FIG. 11. Partial withdrawal of the ostial shuttle, so that the distal portion of the ostial deployment segment remains in the target vessel but the proximal end of the ostial deployment segment is in the aorta.

FIG. 12. Activation of the forward break segment of the ostial deployment segment.

FIG. 13. Advancement of the ostial deployment segment until the forward break segment comes to a stop against the aortic wall.

FIG. 14. Retraction of balloon into the stent deployment segment of the ostial shuttle and stent deployment by expansion of balloon in ostial deployment segment.

FIG. 15. Deactivation of forward break segment prior to withdrawal of assembly from patient.

FIG. 16. Release of a pharmaceutical substance upon expansion of deployment segment (shown in a released configuration in A; and in an expanded configuration in B).

FIG. 17. Deployment segment of ostial stent delivery system with rear break segment in (A) deactivated, and (B) activated, configuration.

FIG. 18. Deployment segment of ostial shuttle showing rear break segment in (A) deactivated, and (b) activated, configuration.

5. DETAILED DESCRIPTION OF THE INVENTION

Ostial stent delivery systems of the invention share the common feature of an ostial deployment segment having a reversibly expandable break segment located adjacent to the stent-bearing region. The break segment, when activated to an expanded configuration, allows the deployment segment to be stably and accurately positioned at the ostium of a target vessel to be stented.

Such systems may be better understood by reference to FIGS. 1-18, which illustrate nonlimiting embodiments of the invention.

FIG. 1 depicts a deployment segment (2) of an ostial stent delivery system (1) showing forward break segment (3), optimally positioned immediately adjacent to the stent-carrying segment, in (A) deactivated (3A) and (B) activated (3B) configuration. The ostial stent delivery system (1) includes a stent (6) crimped on a balloon (11) (prior to deployment) distal to the forward break segment.

FIG. 2 depicts a deployment segment (2) of an ostial shuttle stent delivery system (1) showing forward break segment (3) in (A) deactivated (3C), and (B) activated (3D), configurations. The ostial shuttle stent delivery system (1) includes a tubular catheter (4; distal region only shown), having, at its distal end, a deployment segment (2) comprising, proximal to distal, a forward break segment (3), and an expandable segment (5) on which a stent (6) is mounted.

Figure 1A:
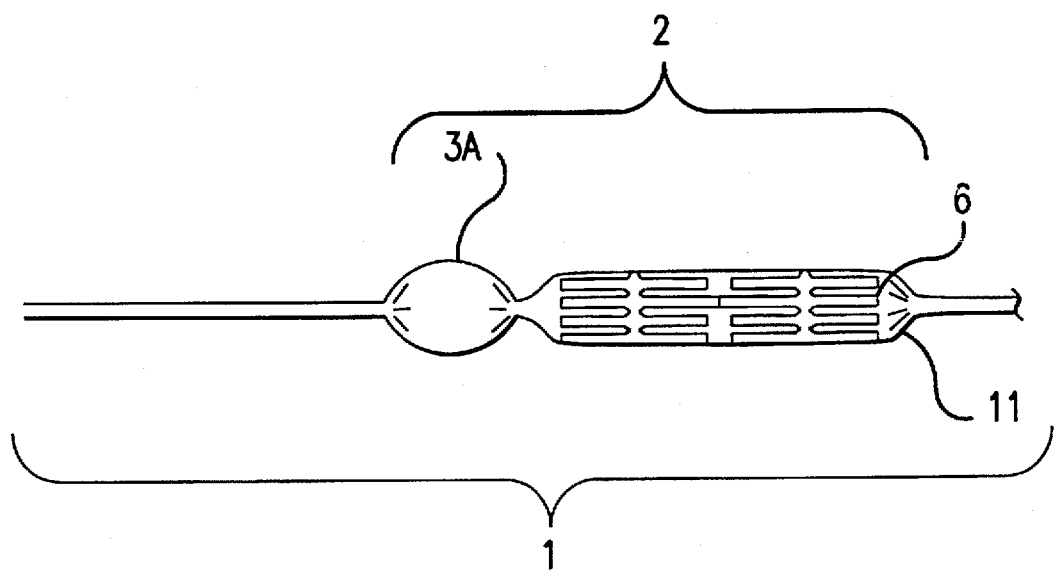

FIGS. 6–15 depict, schematically, a method which may be used for stent placement in an ostial lesion (9) of a target artery (10) branching off a parent conduit vessel (15). In the nonlimiting example depicted, the stent (6) is deployed by expansion of the stent-bearing portion (5) of the deployment segment of an ostial shuttle (2) by a balloon (11) comprised in a balloon catheter (12). In this specific example, an expandable, stent-bearing segment (5A) of the deployment segment (2) is flanked by less-expandable segments (13).

Figure 6:
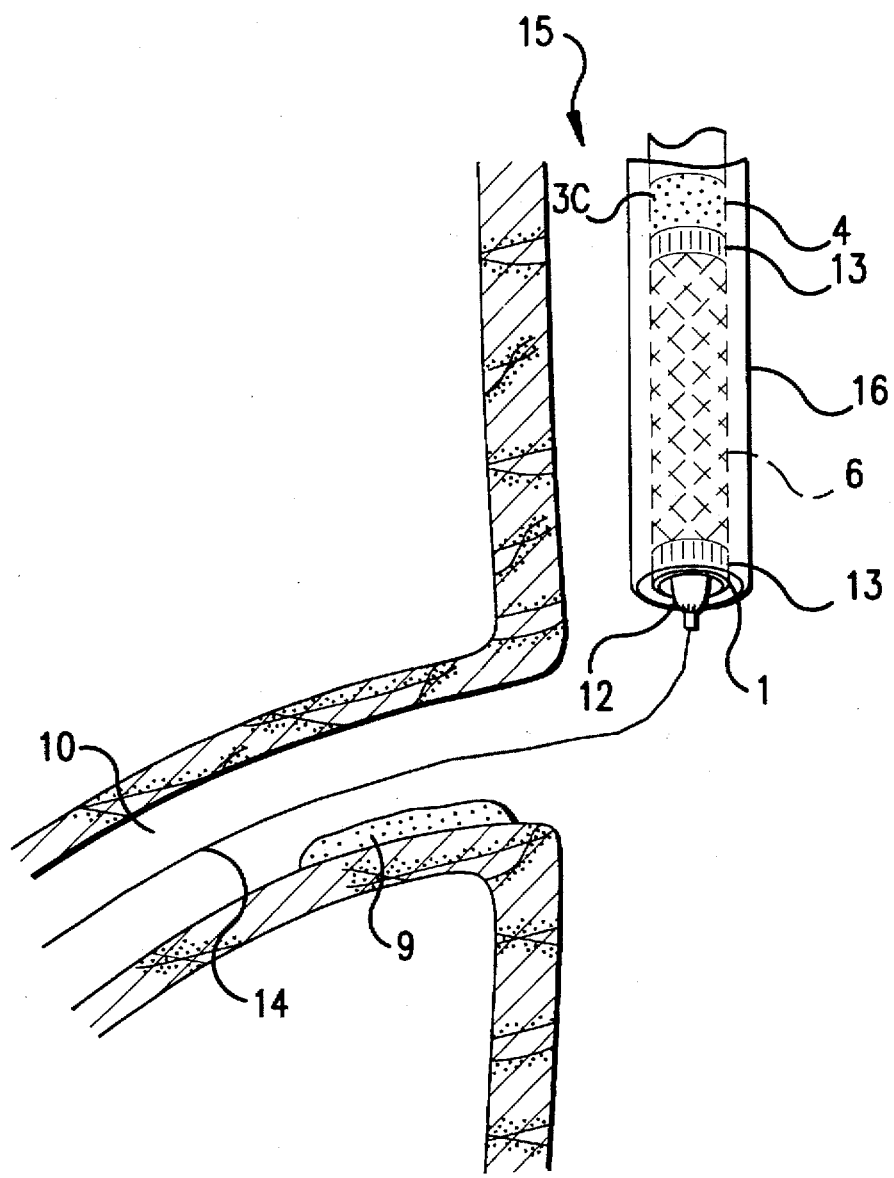

In FIG. 6, a guiding catheter (16), carrying an ostial shuttle delivery system (1) and, within the tubular catheter of the shuttle (4), a balloon catheter (12), has been introduced into the proximity of the ostial lesion (9). A guide wire (14) has been passed, via the guiding catheter (16), through the parent conduit vessel (15) into an artery (10) having an ostial lesion (9).

Figure 7:
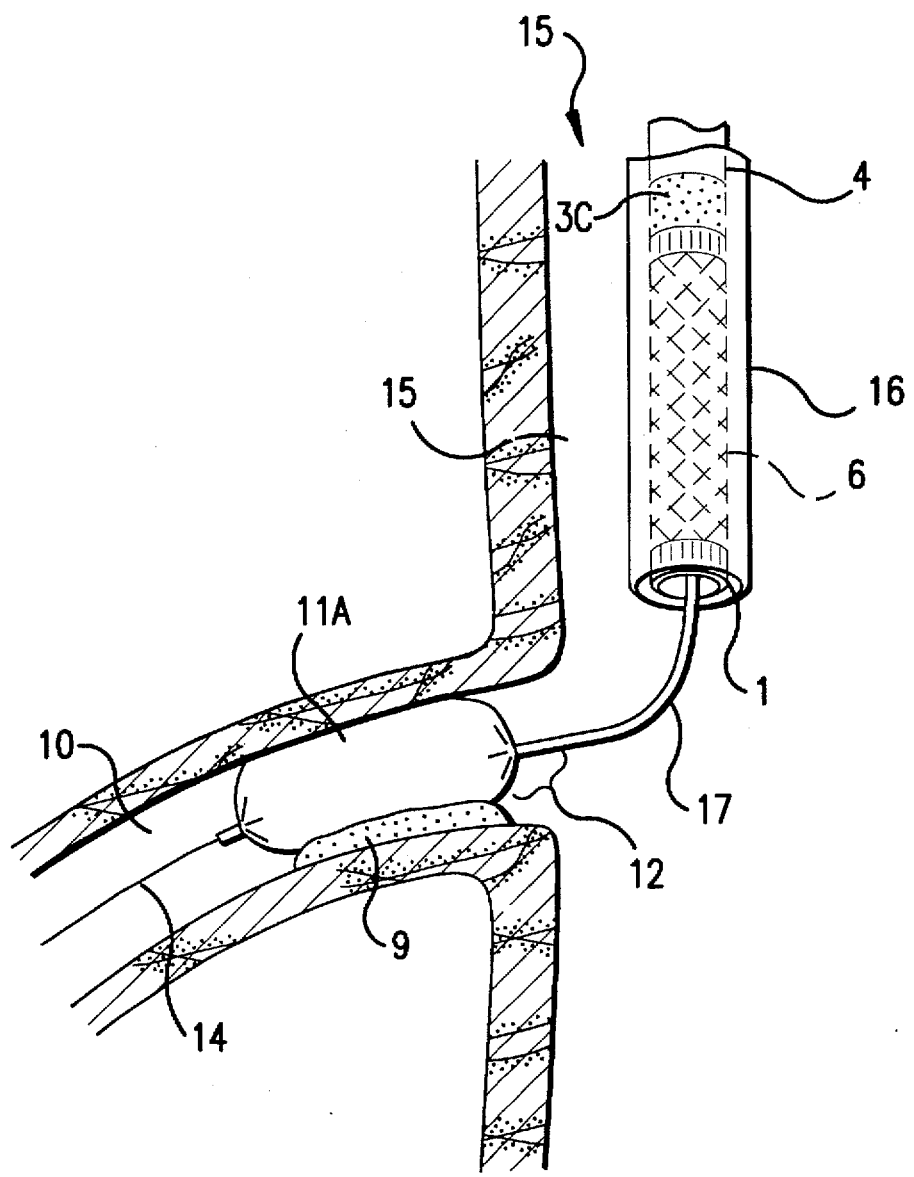

FIG. 7 depicts pre-dilatation of the ostial lesion (9). The balloon catheter (12) has been advanced over the guide wire (14) so that the balloon is located within the ostial lesion (9), and the balloon is inflated (11A).

Figure 8:
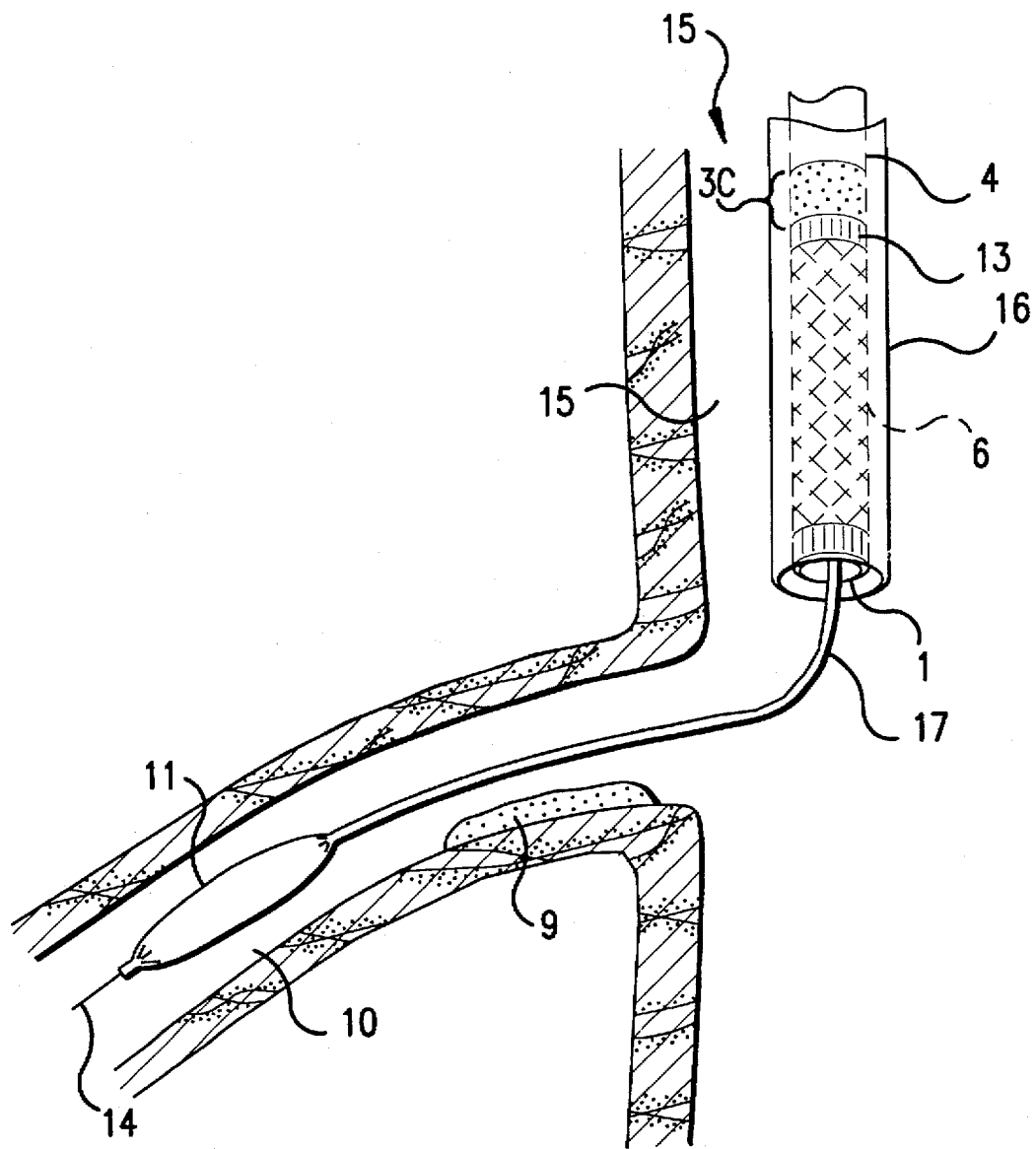

In FIG. 8, the balloon (11) has been deflated and the balloon catheter (12) has been advanced over the guide wire (14) into the artery (10) distal to the predilated ostial lesion (9).

Figure 9:
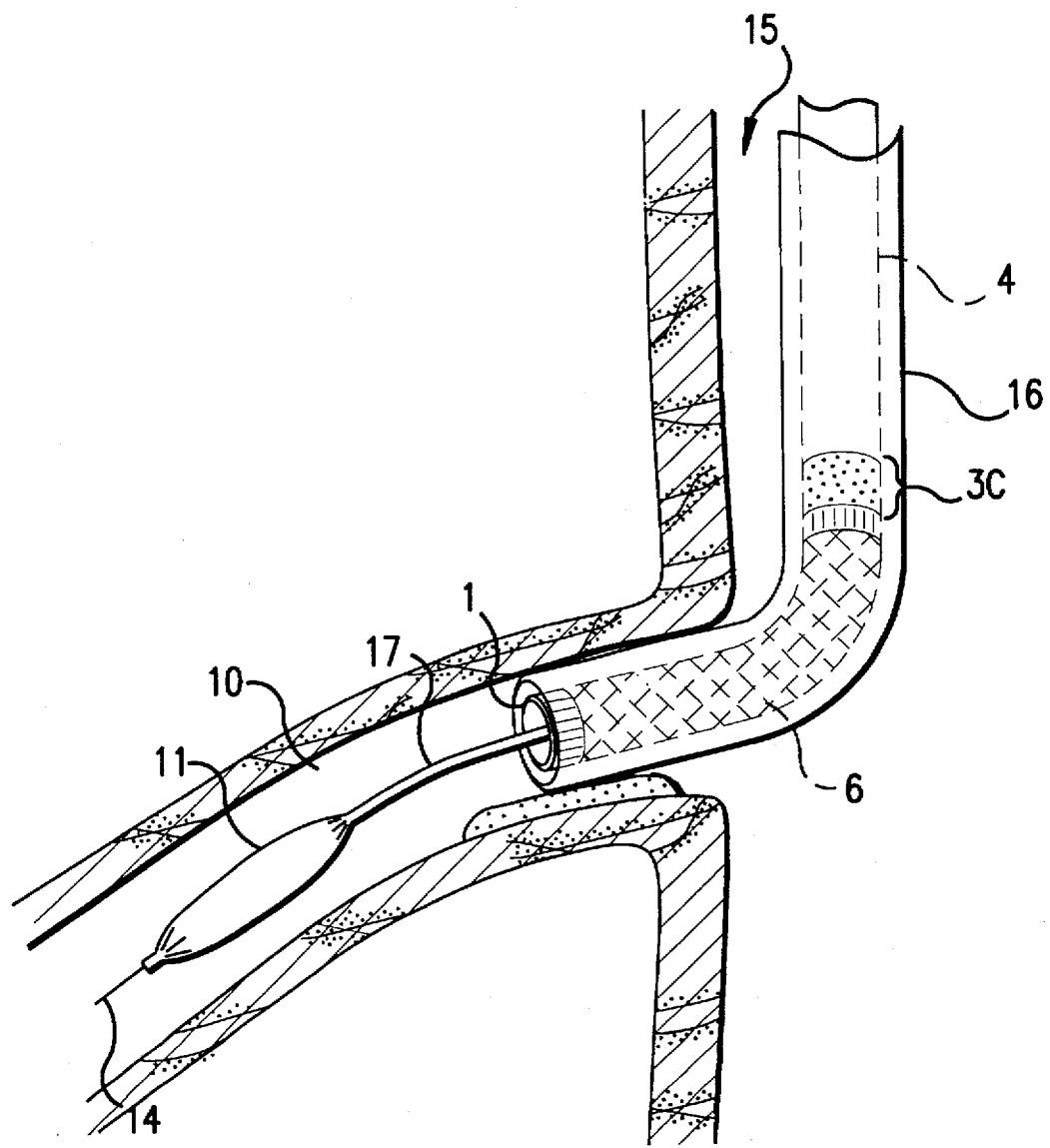

In FIG. 9, the ostial shuttle (1) has been advanced, out of the guiding catheter (16), over the shaft (17) of the balloon catheter (12), into the target artery (10) distal to the ostial lesion (9).

Figure 10:
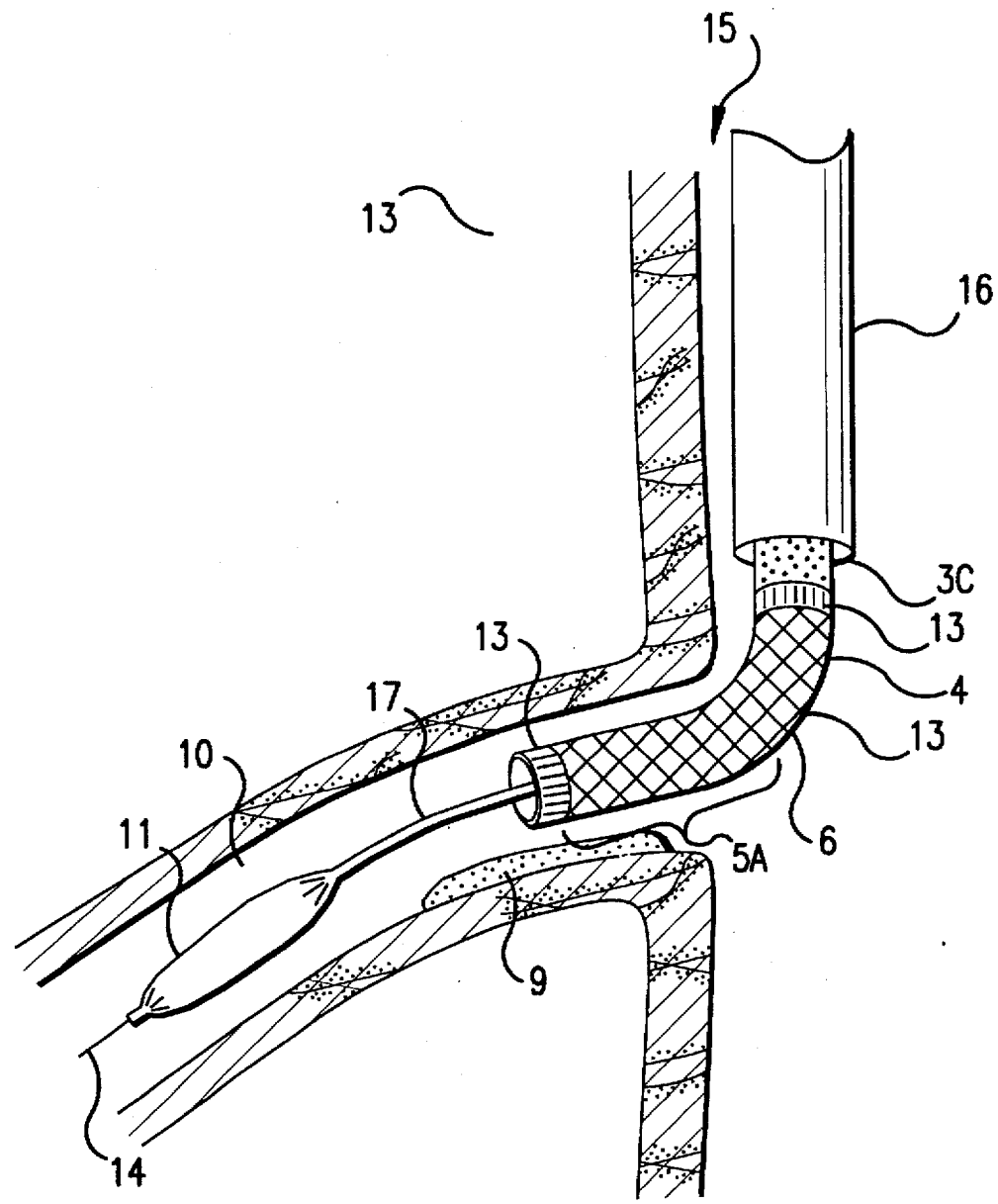

In FIG. 10, the guiding catheter (16) has been withdrawn out of the target artery (10) and into the parent conduit vessel (15). The distal end of the ostial shuttle (1B) remains in the target artery (10).

Figure 11:
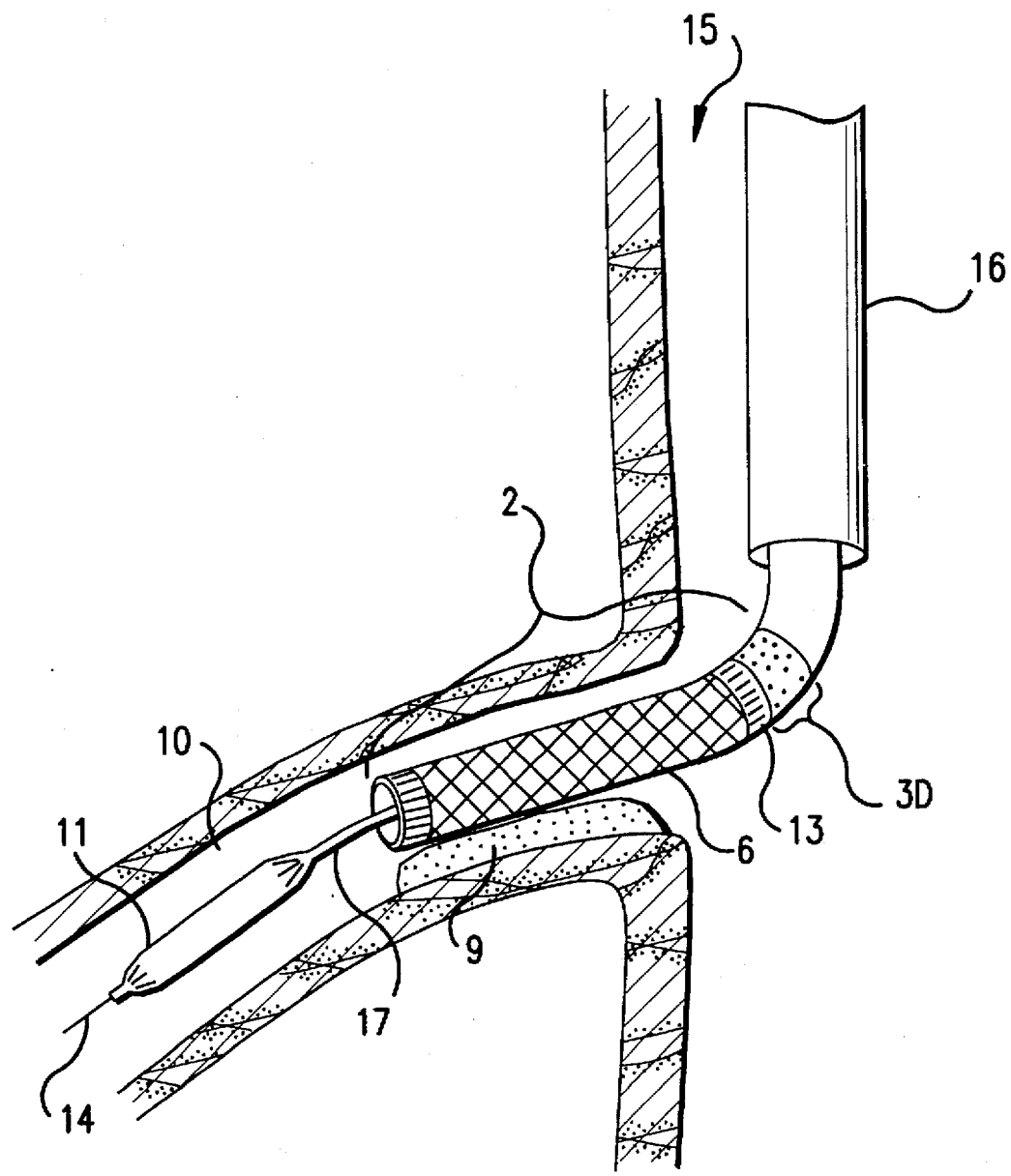

In FIG. 11, the ostial shuttle (1) has been partially withdrawn, so that the distal portion of the ostial deployment segment (2) remains in the target artery but the proximal end of the ostial deployment segment is in the parent conduit vessel (15).

Figure 12:
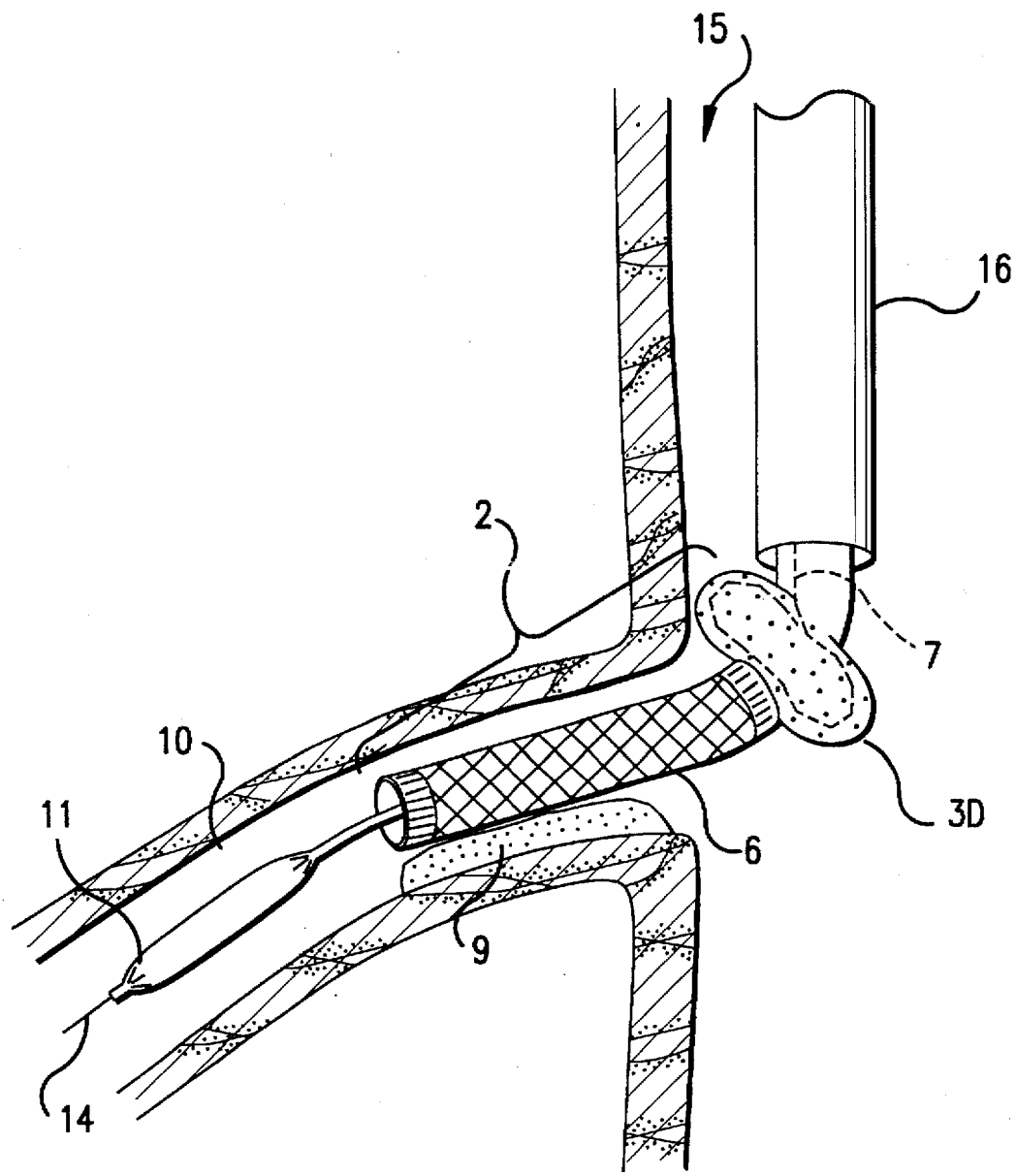

FIG. 12 depicts activation of the forward break segment (3) of the ostial deployment segment (2). Activation is achieved, in this specific nonlimiting example, by inflating a balloon comprised in the forward break segment into activated configuration (3F).

Figure 13:
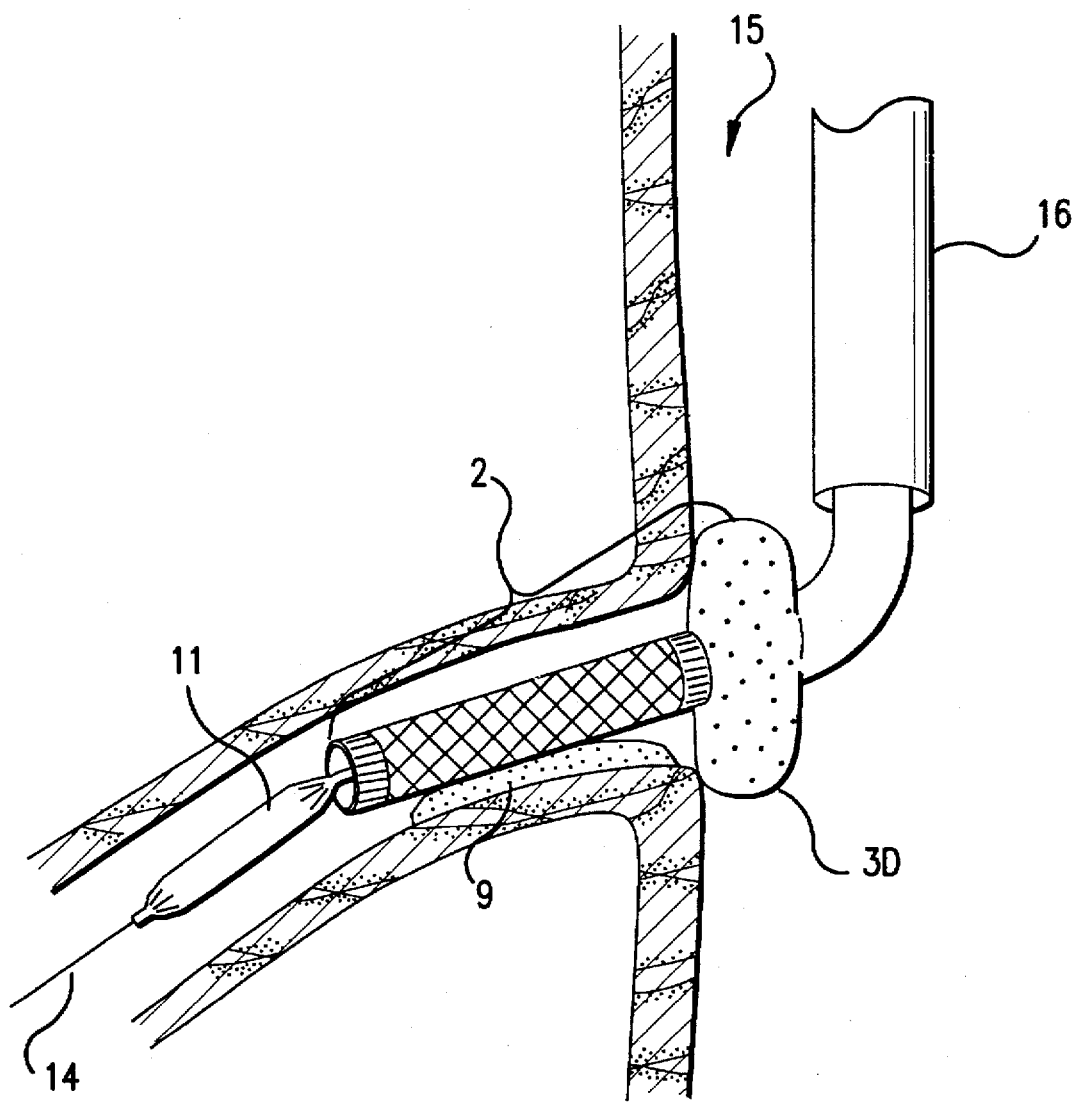

In FIG. 13, the ostial deployment segment (2) has been advanced until the activated forward break segment (3F) comes to a stop against the wall of the parent conduit vessel (15).

Figure 14:
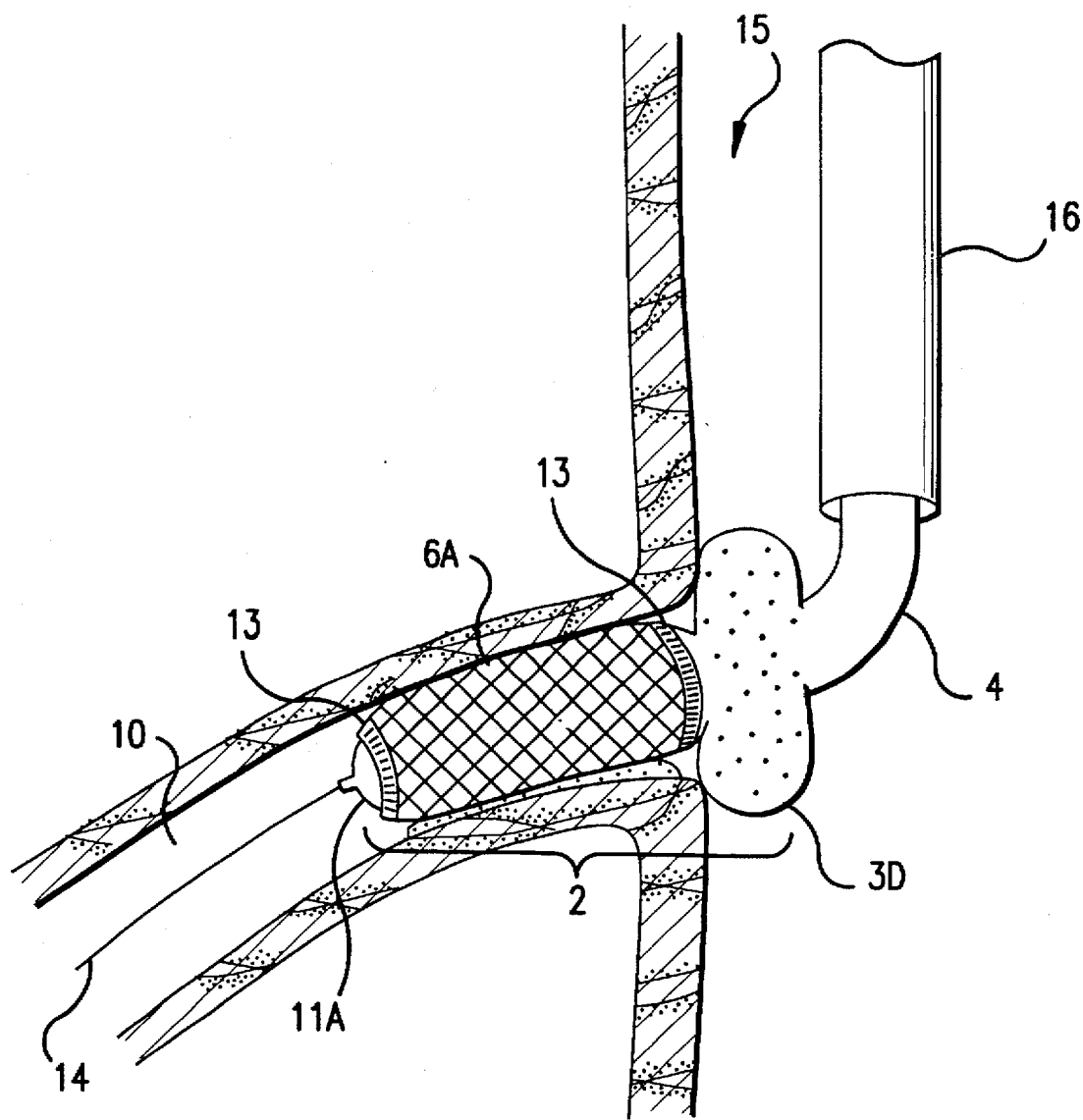

In FIG. 14, stent deployment has been achieved by withdrawing the balloon (11) into the ostial deployment segment (2), and inflating the balloon (11A), thereby expanding the expandable stent-bearing portion (5A) and expanding and deploying the stent (6A). Note that the activated forward break segment (3F) prevents the guiding catheter (16), positioned in the parent conduit vessel (15), from damaging or dislodging the expanded stent (6A).

Figure 15:
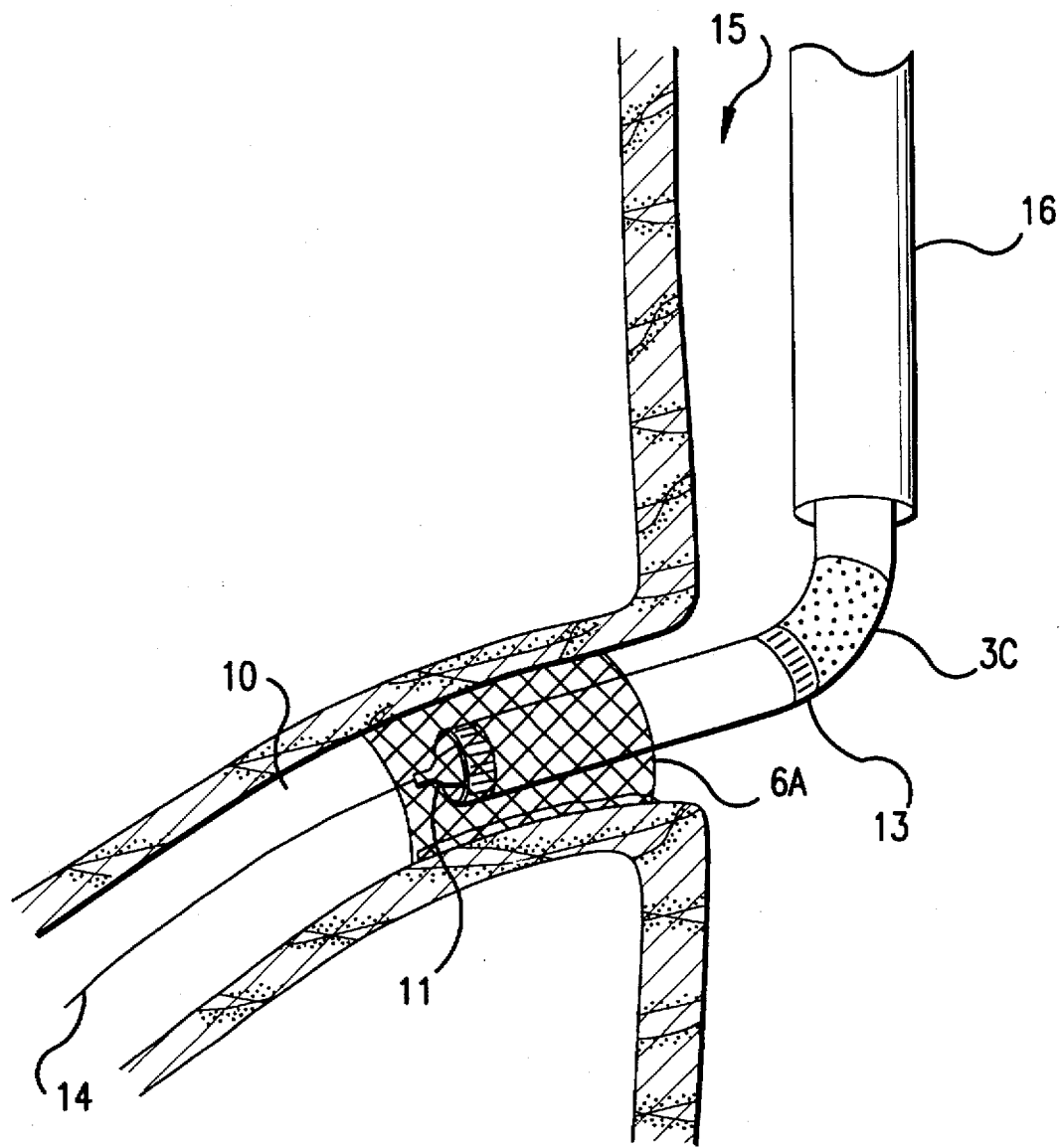

In FIG. 15, the forward break segment has been deactivated (3E) prior to withdrawal of the guide wire (14), balloon catheter (12), guiding catheter (16), and ostial shuttle stent delivery system (1) from the patient.

Figure 16A:
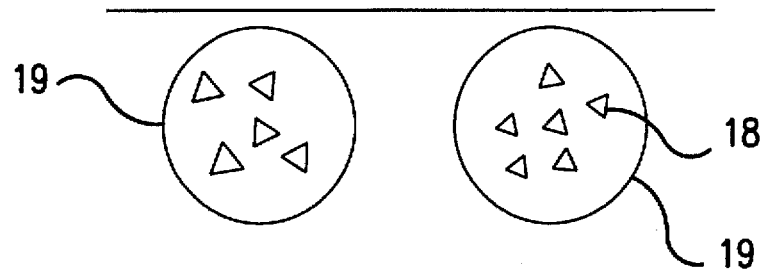
Figure 16B:
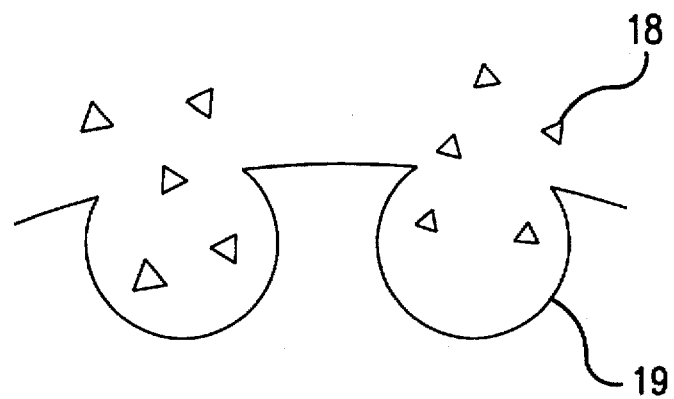

FIG. 16 illustrates, in a magnified view, the release of a pharmaceutical substance (18) represented by triangles, released by the rupture of thin-walled vesicles (19), when the deployment segment (shown in relaxed conformation in A) is expanded (B).

Figure 17A:
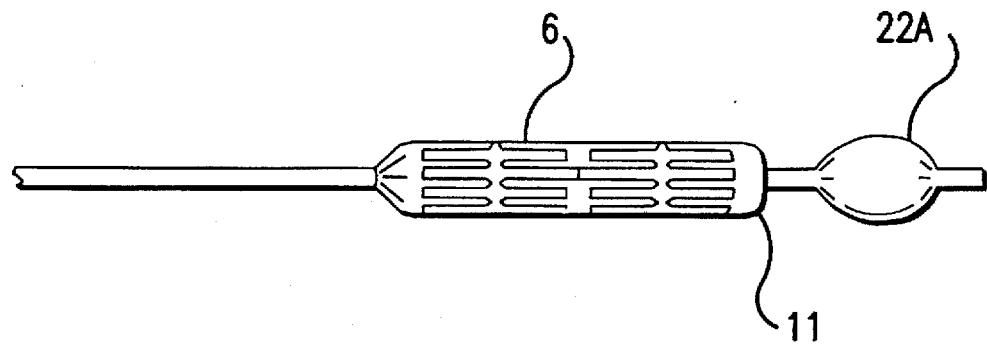
Figure 17B:
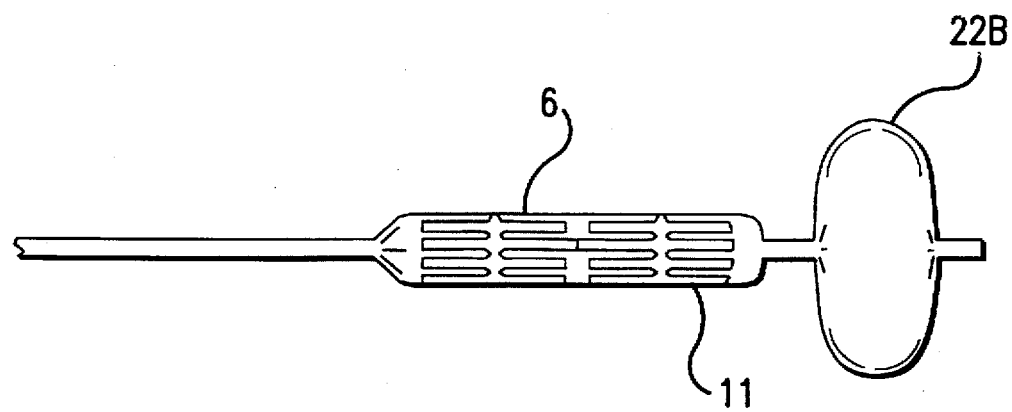

FIG. 17 depicts a deployment segment (2) of an ostial stent delivery system (1) showing a osterior break segment (22) in (A) deactivated (22A) and (B) activated (22B) configuration.

Figure 18A:
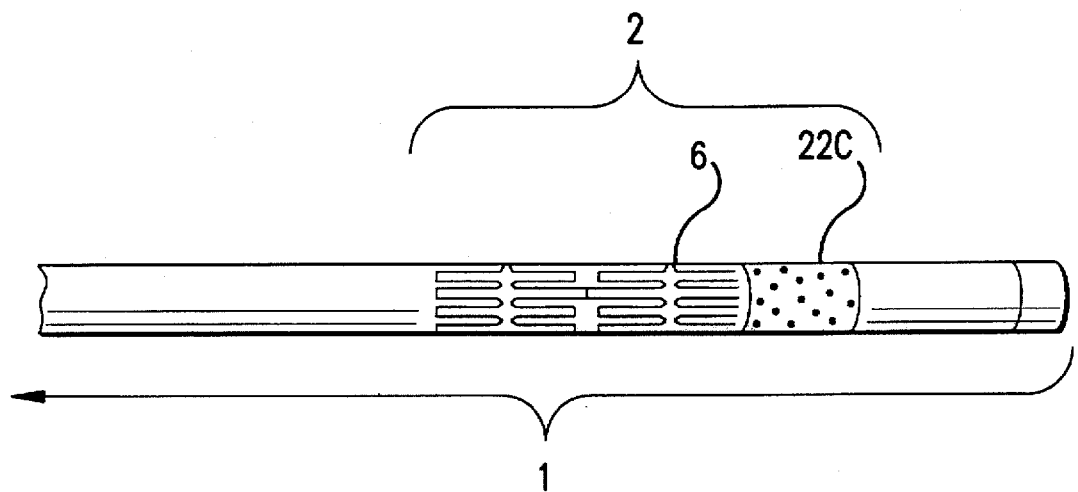
Figure 18B:
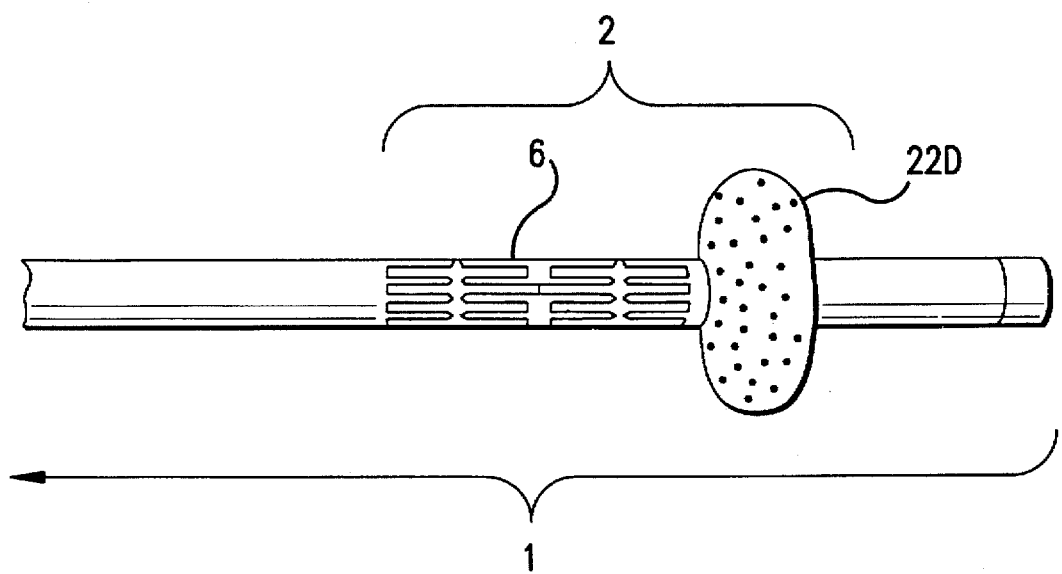

FIG. 18 depicts a deployment segment (2) of an ostial shuttle stent delivery system (1) showing a posterior break segment (22) in (A) deactivated (22C) and (B) activated (22D) configuration.

For purposes of clarity of description, and not by way of limitation, a further detailed description of the invention is divided into the following subsections:

(i) stents;

(ii) break segments;

(iii) shuttles; and (iv) methods of stent placement.

The present invention may be used in vessels or similar conduits wherein a "parent conduit" vessel gives rise to a branch which is a smaller vessel containing an ostial lesion; this smaller vessel is referred to herein as the "target" vessel. The branching of the parent conduit vessel to give rise to the target vessel has a structure which resembles the origin of the coronary arteries from the aorta. For example, the invention may be applied to vessels such as but not limited to, bypass grafts, renal arteries, subclavian or innominate arteries, carotid arteries (or any other vessels arising from the aorta), shunts, bronchial branches, ureters, fallopian tubes, cystic and pancreatic ducts. The invention may also be applied to structures wherein a target vessel containing an ostial lesion opens into a larger space, for example, but not by way of limitation, the urethra (containing an ostial lesion) opening into the bladder.

5.1. STENTS

Stents which may be delivered according to the invention include any vascular or non-vascular stent intended to be placed within a blood vessel (e.g. an artery or vein, including but not limited to a coronary artery, a carotid artery, the aorta and vena cava) or similar structure.

Vascular stents which may be used according to the invention include but are not limited to Palmaz-Schatz, Gianturco-Roubin, Cook, AVE, Strecker, Wiktor, Wallsten and Cordis stents. Stents which may be delivered according to the invention are not limited as to the design, material, length or thickness of the stent, and multiple contiguous or non-contiguous stents may be delivered.

5.2 BREAK SEGMENTS

The break segment of the invention is physically associated with the device on which the stent to be deployed is mounted, so that the break segment, in activated conformation, can be lodged in the ostium, thereby stably retaining the stent in the desired position for deployment. The break segment may be located proximal to (a "forward break segment"), or alternatively, distal to (a "posterior break segment"), the mounted stent. In preferred embodiments, the stent is positioned immediately adjacent to the break segment.

Figure 1B:
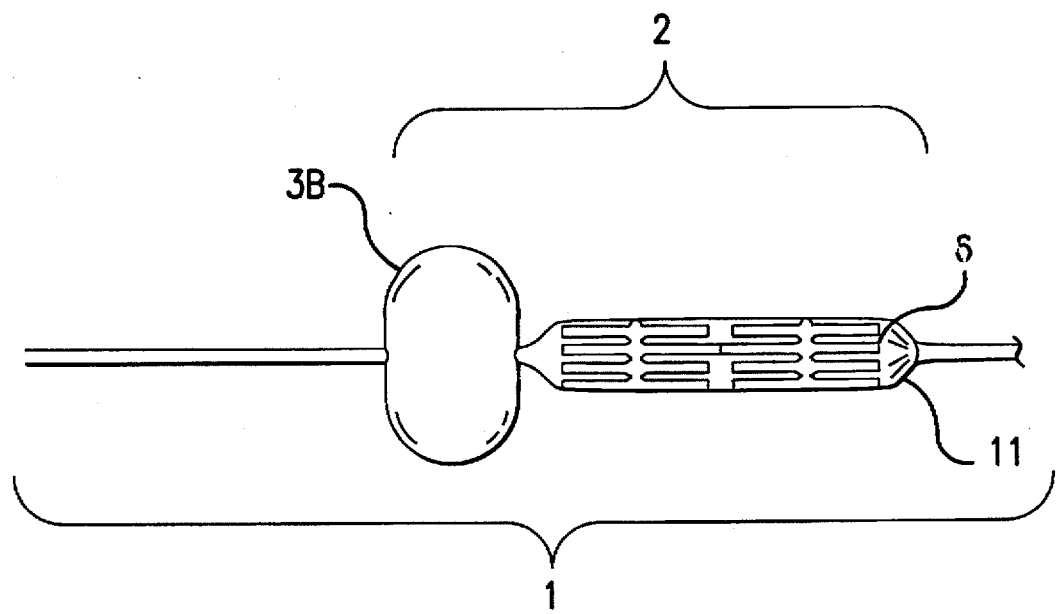

The break segment may be comprised in a shuttle ostial deployment system, as described in the following section 5.3. Alternatively, the break segment may be comprised in any other device used for stent deployment known in the art. For example, where a stent is mounted on a balloon catheter for deployment, the break segment may be comprised in the balloon catheter so as to satisfy the functional criteria set forth above. FIG. 1 depicts a balloon catheter wherein a stent is crimped onto the balloon, comprising a forward break segment in activated and deactivated configurations. FIG. 17 depicts a similar balloon catheter/stent assembly comprising a posterior break segment in activated and deactivated configurations. In both FIG. 1 and FIG. 17, the break segment consists of a balloon which may be inflated to create the activated configuration and deflated so as to create the deactivated configuration.

FIGS. 2–15 and 18 relate to the use of break segments in an ostial shuttle stent delivery system (see Section 5.3, infra.).

The break segment may be fabricated from various materials, depending upon its means on activation. If the means for achieving activation is a separate activating component, such as a nitinol wire or articulated wire, the break segment may be fabricated of a base material which allows the reversible expansion of the activating component, even if the base material is not, itself, activated. In order to permit reversible expansion of such an activating component, the base material should be sufficiently expandable and elastic to permit assumption of the activated configuration and then reversion to the deactivated configuration. For example, but not by way of limitation, the base material of the break segment may be polyethylene or nylon.

Where the break segment is incorporated into a shuttle catheter, the minimum inner radial diameter of the forward break segment has the same size constraints as the shuttle catheter as a whole; namely, it must be large enough to accommodate devices that are to be passed through it. For example, where said shuttle catheter is to be used for stent placement in an ostial lesion of a coronary artery, the inner diameter should be large enough to accommodate the passage of a guide wire and the ancillary means of expansion (e.g., a balloon catheter); in nonlimiting embodiments, the inner diameter may be in the range of from 0.8 to 1.6 millimeters, and preferably from 0.9 to 1.3 millimeters.

Whether the break segment is incorporated into a shuttle catheter or another species of stent delivery system, the maximum outer diameter of the break segment, in deactivated configuration, should also conform to its intended function. For example, where the break segment is to be used in conjunction with stent placement in an ostial lesion in a coronary artery, the outer diameter of the break segment, in deactivated configuration, should be small enough to allow passage into a guiding catheter, and small enough to be safely passed into a coronary artery; in non-limiting embodiments, the outer radial diameter may be in the range of from 1.0 to 2.0 millimeters, and preferably from 1.3 to 1.7 millimeters. When the break segment is activated (expanded), its outer radial diameter may preferably (and not by way of limitation) be increased by 100–300 percent, and more preferably by 200 percent, in order to safely exceed the diameter of the ostium of the target vessel. For example, where the break segment is to be used in stent placement in an ostial lesion of a coronary artery, the outer diameter of the break segment, in activated configuration, may be in the range from 2.0 to 6.0 millimeters and preferably from 3.0 to 5.0 millimeters.

In one specific, nonlimiting embodiment of the invention, the break segment comprises a balloon which may be inflated to achieve an activated configuration and deflated to achieve a deactivated configuration. Such a break segment may be comprised within a balloon catheter upon which a stent may be mounted prior to deployment, as depicted in FIGS. 1 and 17. In such embodiments, the break segment may be activated by, for example but not by way of limitation, inflation using a separate means (e.g., a separate air conduit) from that used to inflate of the balloon catheter. Alternatively, such a break segment may be comprised in a shuttle stent delivery system, as illustrated in FIGS. 3 and 6–15.

In another specific, nonlimiting embodiment of the invention, the activating component is a nitinol wire comprised in the break segment. The nitinol wire is configured such that, upon passage of current through the nitinol wire, the diameter of the break segment expands. For example, the nitinol wire may be configured in a loop (see, for example, FIG. 4) or coil positioned such that the central axis of the loop or coil is parallel with, or coincident with, the central axis of the break segment. Accordingly, the inner diameter of the loop or coil has the same minimum size constraints as the stent placement devise employed. The nitinol wire may be embedded within an elastic base material, as described above. Alternatively, the nitinol wire may on activated configuration, expand freely from the stent delivery system and in deactivated configuration, may return to its original dimensions. According to these embodiments, the ostial shuttle stent delivery system comprises a means for activating the nitinol wire by passing a current through the nitinol wire. Although a number of means of creating such current would be known to the skilled artisan, as a nonlimiting example, the current may be supplied via a battery.

In another specific, nonlimiting embodiment of the invention, the activating component may comprise an articulated wire. The articulated wire may be configured such that it may be bent at the articulation to increase the diameter of the forward break segment (for example, see FIG. 5). Preferably, at least two such wires may be comprised in the ostial shuttle. In one specific, nonlimiting example, the articulated wire may be brought into its angular configuration by pushing its proximal end while pulling on its distal end, for example, by a retention wire (see FIG. 5). The articulated wire may be fabricated from stainless steel, titanium, or nitinol. It may preferably have a length of 150 to 300 cm.

5.3. SHUTTLES

According to one nonlimiting series of embodiments, the invention may utilize a shuttle stent delivery system:

As described in pending U.S. patent application Ser. No. 08/430,378, the entirety of which is hereby incorporated herein by reference, a "shuttle" stent delivery system provides the benefits of an optimal three-step stent placement procedure using multiple balloons but obviates the need for balloon exchanges. The system utilizes a tubular stent delivery catheter (herein referred to as a "shuttle") comprising a deployment segment having an expandable portion, onto which a stent may be mounted in a contracted conformation. The deployment segment is not expanded by means intrinsic to itself, but rather is expanded by ancillary means, for example, by a balloon catheter separate and distinct from the shuttle. Multiple balloon changes are rendered unnecessary because the structural design of the deployment segment supplies the optimal physical characteristics offered by multiple balloons.

In particular embodiments of the shuttle stent delivery system, the shuttle comprises a deployment segment having an expandable portion over which a stent is mounted in contracted condition. The stent-bearing expandable portion of the deployment segment is flanked by segments which are not expandable to the same degree as the stent-bearing portion. Optionally, the deployment segment comprises a releasable biological, pharmaceutical, or structural substance.

For stent placement in a partially occluded blood vessel (or similar structure) in a patient, a guide wire, having a length greater than the balloon catheter, may be introduced into the vessel. A shuttle with an expandable stent mechanically or by other means attached onto the deployment segment in contracted condition, may be mounted coaxially over the shaft of the balloon catheter outside the patient. The shuttle may be designed to be coaxially mounted over the shaft of the balloon catheter over the entire length of the shuttle (hereafter referred to as an "over the catheter" shuttle) or only over a distal segment of the shuttle comprising the deployment segment (hereafter referred to as a "monorail" shuttle). For the over-the catheter shuttle, the balloon catheter used has a length greater than the shuttle. The balloon catheter is designed such that the balloon is reliably and repeatedly capable of advancing in unexpanded (i.e., never inflated) or collapsed (i.e., inflated at least once and then deflated) condition through the entire length of the shuttle and in and out of the distal end of the shuttle.

The occluded region of the vessel may then be predilated using the balloon catheter. Then, without withdrawing the balloon catheter from the patient, the balloon may be deflated and advanced beyond (distal to) the occlusion, and the shuttle, fitting over the shaft of the balloon catheter, may be positioned such that the stent-bearing deployment segment is positioned within the pre-dilated occluded portion of the vessel. The balloon may then be pulled back into the deployment segment of the shuttle, and expanded to high pressures. Expanding the balloon accomplishes deployment of the stent, and also offers the benefits of post-dilatation. The need for a separate, shorter, post-dilatation balloon should be obviated by the relatively non-expandable segments flanking the expandable region of the deployment segment, which protect the vessel adjacent to the stent from damage. Moreover, releasable substances comprised in the deployment segment may be liberated by the expansion of the deployment segment via inflation of the balloon. Following stent deployment, the balloon may be deflated and the stent delivery and balloon catheters may be removed from the patient.

The shuttle stent delivery system may be used for the placement of either non-self-expanding or self-expanding stents in blood vessels or similar structures. Moreover, the system may be used to deploy multiple stents in a single procedure, and may be used in conjunction with an anti-embolic filter.

Figure 2A:
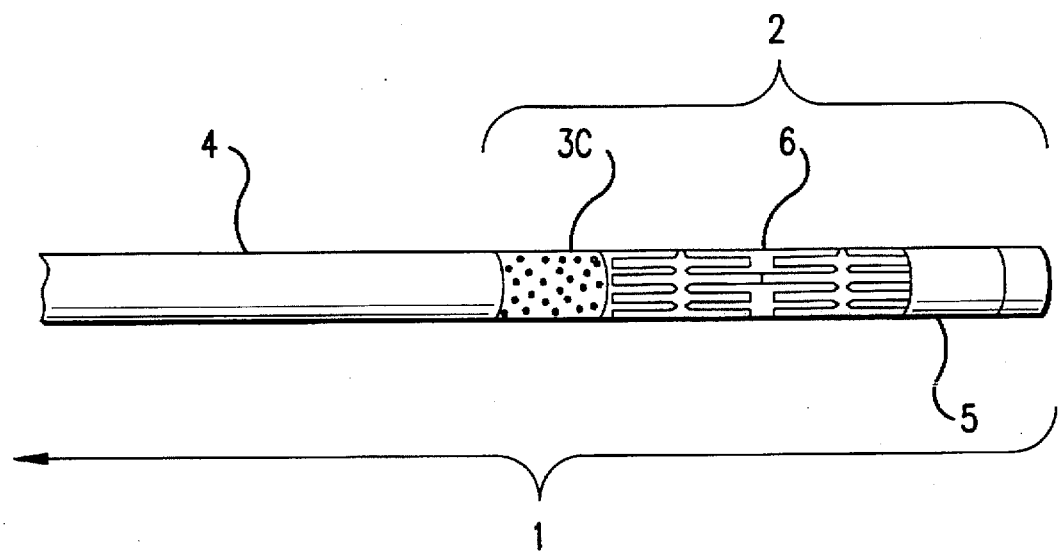
Figure 2B:
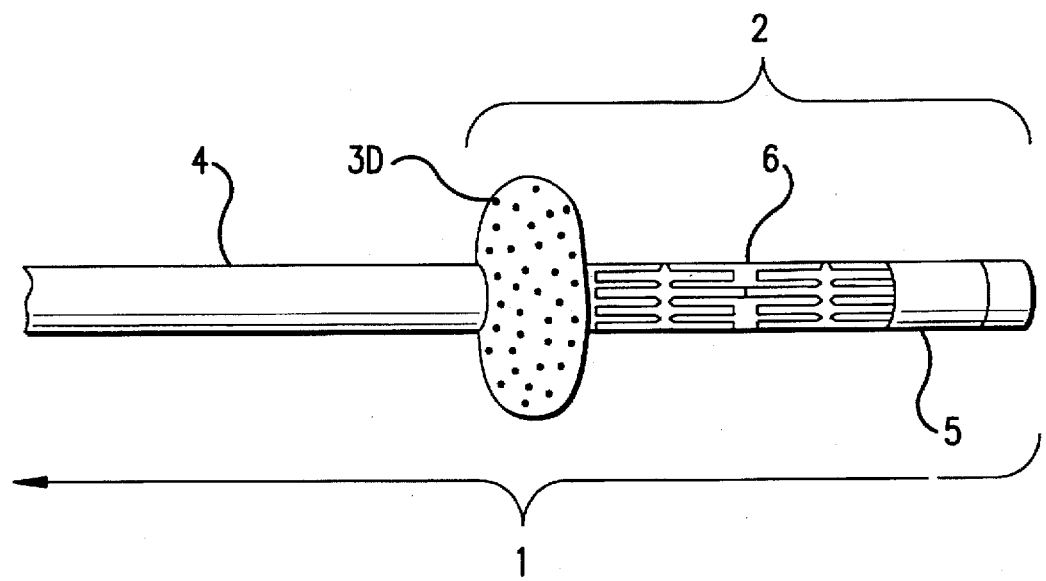
Figure 3A:
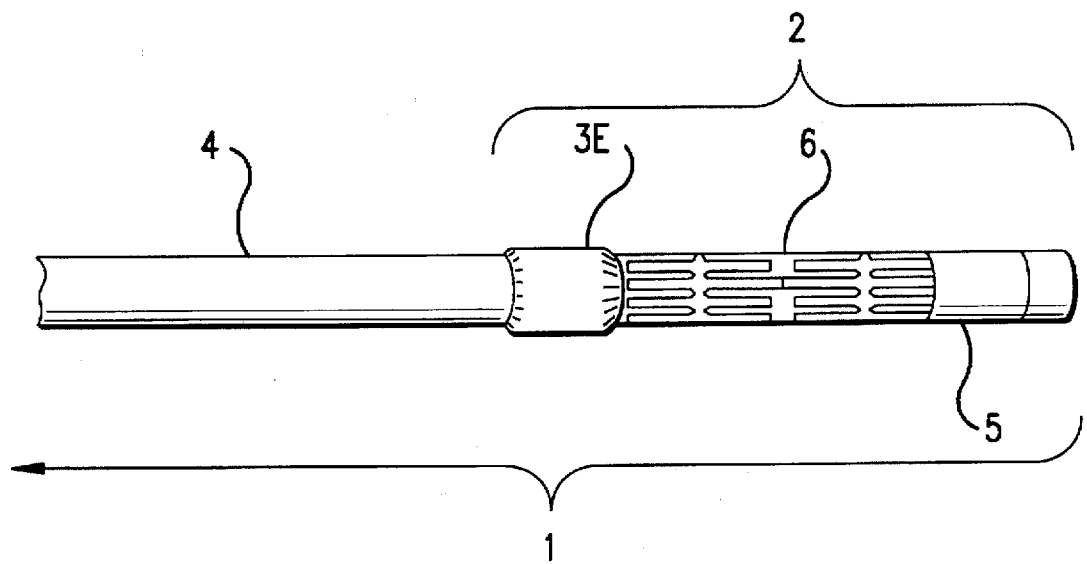
FIG. 3 depicts a deployment segment (2) of an ostial shuttle stent delivery system (1), as in FIG. 1, wherein the mechanism of activation of the forward break segment (3) is a balloon, in (A) deactivated (3E) and (B) activated (3F) configurations.
Figure 3B:
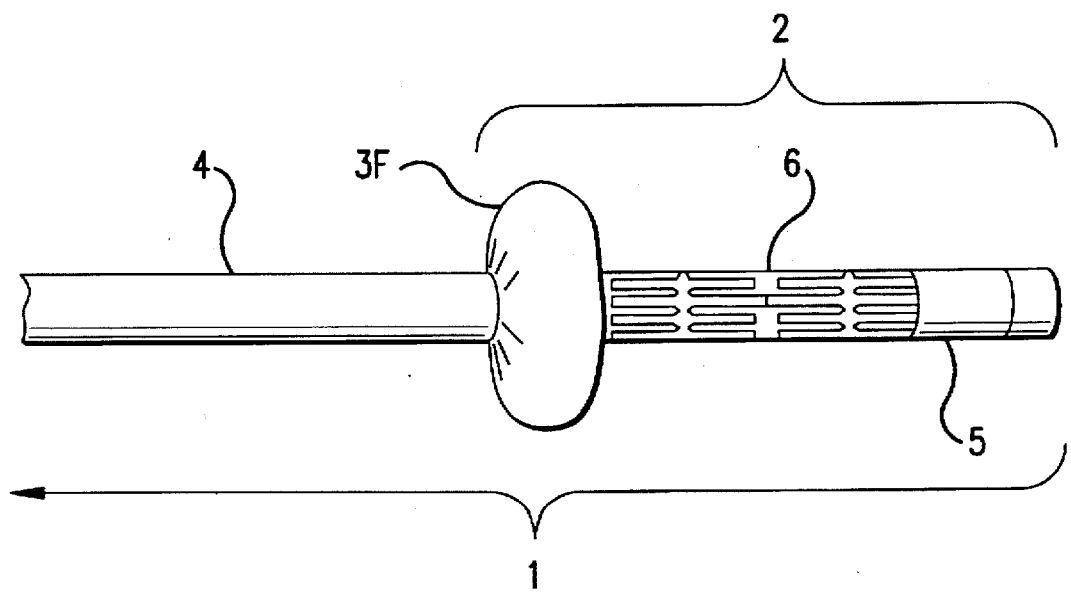
Figure 4A:
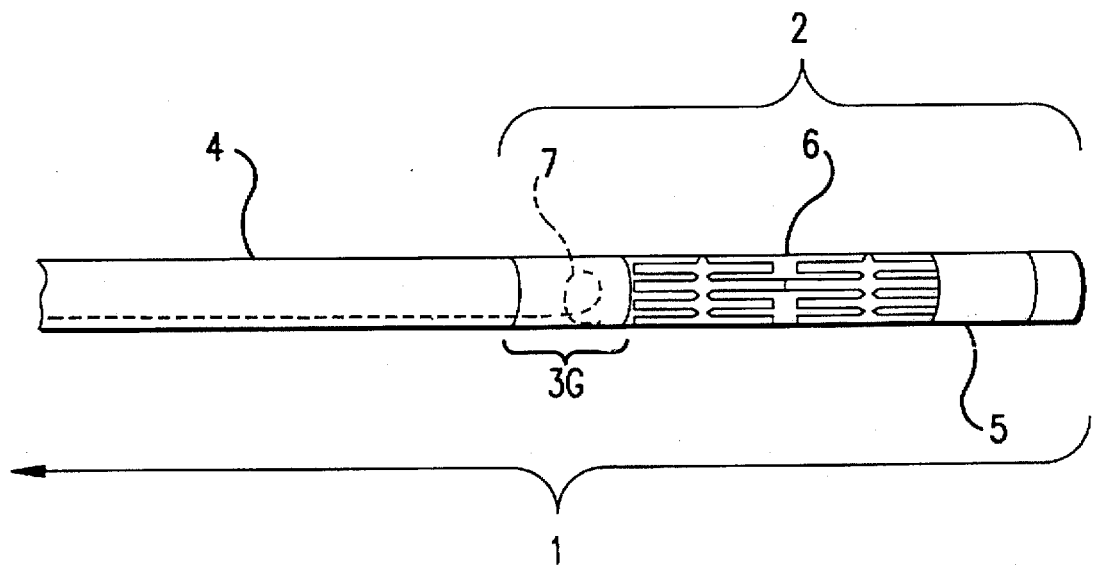
FIG. 4 depicts a deployment segment (2) of an ostial shuttle stent delivery system (1), as in FIG. 2, wherein the mechanism of activation of the forward break segment (3) is a nitinol wire loop (7), showing the forward break segment in (A) deactivated (3G), and (B) activated (3H), configurations.
Figure 4B:
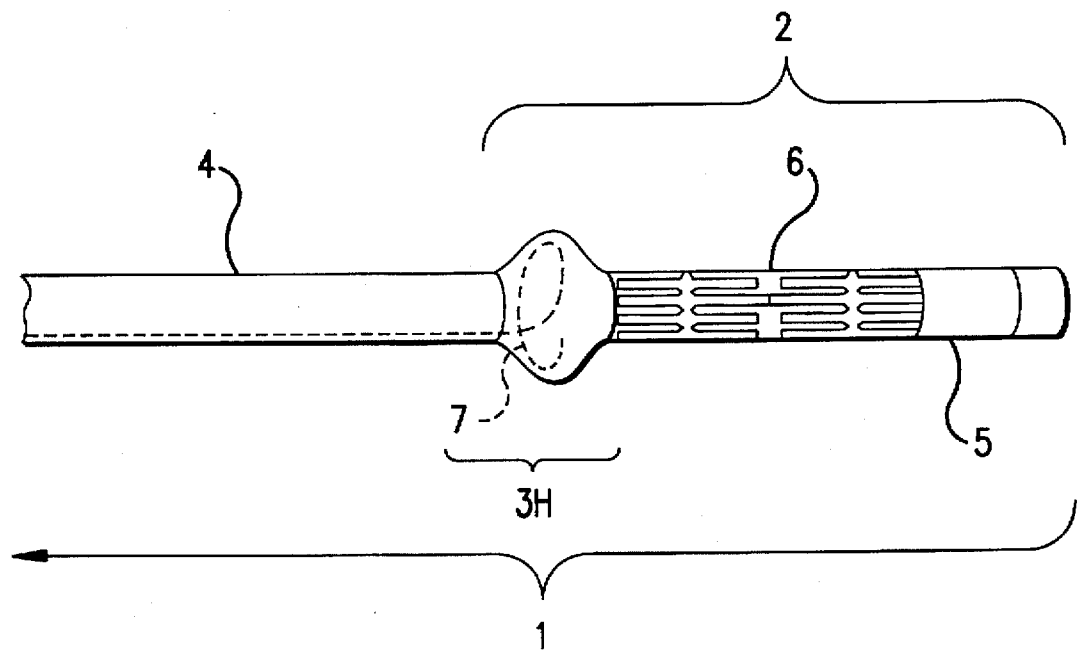
Figure 5A:
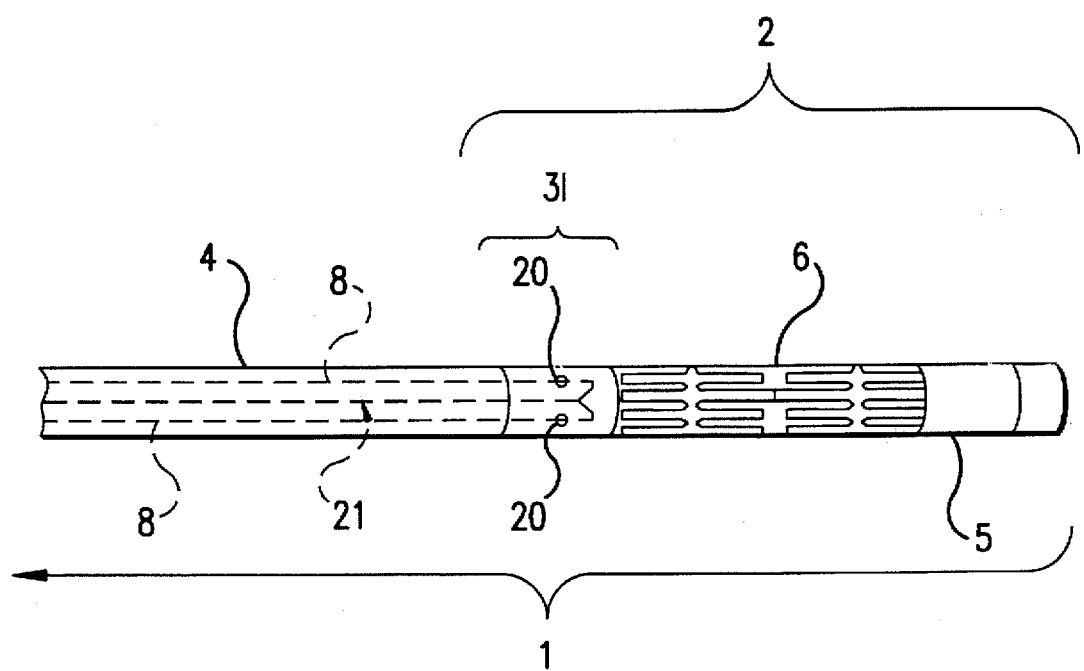
FIG. 5 depicts a deployment segment (2) of an ostial shuttle stent delivery system (1), as in FIG. 2 wherein the mechanism of activation of the forward break segment (3) is a pair of articulated wires (8) having articulations (20) and attached to a longitudinally placed retention wire (21), showing the forward break segment in (A) deactivated (3I), and (B) activated (3J), configurations.
Figure 5B:
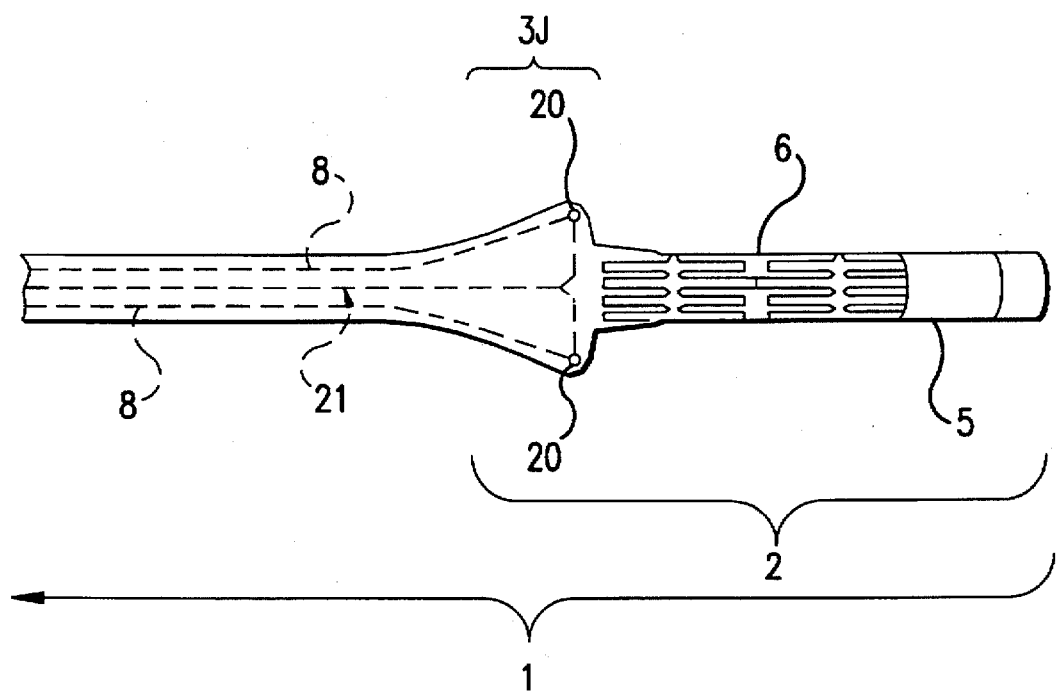

An ostial shuttle stent delivery system, according to the invention, is a species of tubular catheter (also referred to as a "shuttle catheter") having a distal and a proximal end, wherein the proximal end may preferably be kept outside of the patient (thereby allowing the operator to adjust the position of the stent during placement) and comprising an ostial deployment segment (used for carrying and deploying the stent or stents) located at the distal end (preferably, within 2–3 cm of the distal end of the shuttle catheter). A specific example of the distal end of such a shuttle is depicted in FIG. 2.

In one nonlimiting embodiment, the present invention relates to an ostial shuttle stent delivery system for delivering a stent in a vessel having an ostial lesion in a patient in need of such treatment, comprising a tubular catheter having, at its distal end, an ostial deployment segment comprising (a) in the proximal region of the ostial deployment segment, a forward break segment capable of reversible expansion; and (b) in the distal region of the deployment segment, an expandable portion onto which a stent is mounted.

Alternatively, the ostial shuttle stent delivery system may comprise a tubular catheter having, at its distal end, an ostial deployment segment comprising (a) in the proximal region of the ostial deployment segment, an expandable portion onto which the stent is mounted; and (b) in the distal region of the ostial deployment segment, a posterior break segment capable of reversible expansion.

The shuttle catheter may be fabricated from a variety of materials, including, but not limited to, polyethylene, nylon, and nitinol, which are the preferred materials for the placement of stents in blood vessels. The length and radial diameter of the shuttle catheter may vary depending upon the vessel or similar structure into which the stent is to be placed.

For example, but not by way of limitation, the approximate longitudinal length of the shuttle catheter for placement of a stent into a coronary artery may be in the range of from 80 to 140 centimeters, and preferably from 90 to 125 centimeters, the outer radial diameter may be in the range of from 1.0 to 2.0 millimeters, and preferably from 1.3 to 1.7 millimeters, and the inner radial diameter may be in the range of from 0.8 to 1.6 millimeters, and preferably from 0.9 to 1.3 millimeters. The radial diameters are temporarily expanded in embodiments where stent deployment is effected by an ancillary means of expansion.

The ostial deployment segment of the shuttle comprises one or more expandable portions, onto which one or more stents may be mounted (e.g., compacted) prior to placement in a patient. Where the stent is to be deployed using expansion by an ancillary means, such as the inflation of a separate balloon, the stent may be mounted on an expandable segment which, in preferred embodiments of the invention, is flanked by segments (called "flanks") which are not expandable or are less expandable than the expandable portion. These less-expandable flanks protect the vessel walls adjacent to the lesion from damage during stent deployment.

For conventional stents in use for treatment of coronary arteries, the length of an expandable portion may be, for example, and not by way of limitation, in the range of from 5 to 35 millimeters, and preferably from 9 to 30 millimeters.

The expandable portion and flanks may be fabricated of different materials, having different expandabilities. Alternatively, the expandable portion may be made of the same material as the remainder of the shuttle, and the flanks may be created by placing two short tubular portions of reinforcing material at the boundaries of the expandable portion, or by other means known in the art.

Markers, for example radiopaque markers such as gold, tantalum or platinum markers may be placed at the distal ends of the stent-bearing region of the shuttle, or at the location of the break segment and/or at the boundaries between an expandable portion and its flanks or between the flanks and the remainder of the shuttle to aid in stent positioning.

One or more stent(s) may be compacted onto the expandable portion or portions of the ostial deployment segment prior to placement in the patient. For non-self-expanding stents, such as, for example, a Palmaz-Schatz stent, the stent may simply be crimped onto an expandable portion of the deployment segment. For self-expanding stents, the stent may be retained in non-expanded form on the shuttle by a restraining mechanism. For example, constraining sleeves may extend over both edges of the stent, retaining it in place until the sleeves are pulled apart by expansion of the expandable portion of the deployment segment. In the case of self-expanding or non-self expanding stents, the shuttle may optionally comprise a protective sheath which may cover the stent prior to deployment; such a sheath may be removed by retracting it by pulling on its proximal end, which may be kept outside of the patient at all times.

In certain, nonlimiting embodiments of the invention, biological, pharmaceutical, and/or structural materials may be incorporated into the ostial deployment segment of the ostial shuttle, such that these materials may be released upon expansion of the deployment segment by an ancillary means. For example, such materials may be incorporated into thin-walled vacuoles near the surface of the deployment segment closest to the wall of the vessel or similar structure into which the stent is to be placed, such that the vacuoles may rupture, releasing their contents, when the deployment segment is expanded. As another example, a biodegradable polymer layer with antithrombotic and/or antiproliferative properties may be incorporated into the ostial stent delivery catheter either over the mounted stent or between the stent and the expandable portion of the ostial deployment segment. When the deployment segment and the stent are expanded, this layer may be released from the shuttle while remaining attached to the stent in the treatment site. Materials which may be incorporated into the deployment segment include, but are not limited to, anti-coagulants such as heparin, hirudin, hirulog, or platelet receptor inhibitors, thrombolytic agents such as tissue plasminogen activator, compounds that deter the proliferation of vascular smooth muscle cells (thereby decreasing the likelihood of restenosis) such as radioactive compounds, anti-CD41 antibodies or antisense oligo-deoxynucleotides, radiopaque materials such as iodine or barium salts, structural materials such as fibrin layers, endothelial cells, segments of veins or arteries or synthetic grafts such as dacron. It should be noted that incorporation of such materials into the deployment segment, with consequent local release at the site of stent placement, may decrease or eliminate the need for systemic administration of such agents or other adjunct therapies. For example, the need for aggressive systemic anti-coagulation may be decreased, thereby diminishing the likelihood of hemorrhagic complications at the vascular access site.

The tip of the ostial shuttle catheter may, in nonlimiting embodiments, comprise a means for reversible expansion (such as a nitinol wire) to facilitate withdrawal of the ancillary means of expansion into the shuttle catheter for stent deployment and for removal from the patient.

In further nonlimiting embodiments of the invention, the ostial shuttle catheter may comprise, at its distal tip, a structure or structures capable of forming one or more antiembolic filters, with fenestrations large enough to permit the passage of blood or other fluid, but small enough to trap debris (such as fragments of thrombus or atherosclerotic plaque) freed during pre-dilatation or stent deployment. The filter may be capable of fitting over, for example, a balloon catheter shaft or guidewire, and may be capable of expansion by intrinsic or ancillary means. For example, an intrinsic means of expansion would include a filter constructed of a thermal memory alloy such as nitinol, which may be expanded by a weak electrical current. As an example of an ancillary means of expansion, a balloon may be used to expand the filter. In either case, the filter and distal region of the ostial shuttle catheter may desirably be constructed such that the filter may be advanced distal to the obstructed region of the vessel and expanded prior to pre-dilatation and stent deployment. The filter itself may preferably be sufficiently flexible, by virtue of the material of which it is made or its construction, to permit pull-back of the entire delivery system following stent deployment, with the filter in its expanded shape.

In a non-limiting example, an embolic filter is comprised in a separate element, wherein the filter (for example, a coiled structure) is positioned distal to the distal tip of the shuttle catheter, and is connected to a small diameter shaft running through the shuttle catheter and extending its proximal end outside of the patient, to permit manipulation by the operator (e.g. forward advancement, retention, and withdrawal).

In a specific non-limiting embodiment of the invention, such an embolic filter may have an alterable configuration; for example, the filter may be constructed of nitinol, and have a first conformation which is a straight wire. Upon the passage of electrical current, this straight wire may assume a second conformation which is an inverted conical spiral of preset maximal diameter.

For stent placement, the ostial deployment segment of the shuttle catheter may be placed over the shaft of an ancillary means of expansion, such as a balloon catheter. This may be advantageous, as the delivery of stents may be improved (relative to placement over a guide wire) by the use of more rigid and larger diameter shafts as guiderails for advancing the ostial deployment segment assembly into the desired position. The shuttle catheter may be coaxial with the ancillary means of expansion over the entire length (termed an "over the catheter shuttle") or over the distal segment of the ostial shuttle catheter comprising the ostial deployment segment (termed a "monorail shuttle").

The shuttle ostial stent delivery system of the invention provides for an ancillary means of expanding the ostial deployment segment of the shuttle. While means of expansion other than a balloon catheter are envisioned (such as, for example, a nitinol wire, the distal segment of which is made to become a coil of a predetermined diameter when placed within the expandable deployment segment of the shuttle and when a weak electrical current is passed through such a nitinol wire) this ancillary element will be exemplified by and referred to hereafter as a balloon catheter.

The balloon catheter may be fabricated from a variety of materials, including, but not limited to, polyethylene and nylon, which are the preferred materials for the placement of stents in blood vessels.

As described above with relation to the shuttle, the length and radial diameter of the balloon catheter may vary depending upon the vessel or similar structure into which the stent is to be placed. For example, the approximate length of the shaft of a balloon catheter for placement of a stent into a coronary artery may be in the range of from 80 to 140 centimeters, and preferably from 90 to 125 centimeters, and the radial diameter of the shaft portion may be in the range of from 0.8 to 1.6 millimeters, and preferably from 0.9 to 1.3 millimeters.

The balloon portion of the balloon catheter may desirably be structured such that the balloon is capable of repeatedly and reliably advancing in unexpanded condition as well as in collapsed condition through the entire length of the shuttle, and in and out of the distal ends of the shuttle. For example, in order to achieve these goals, the balloon may preferably be a non-compliant high-pressure balloon with longer tapered ends and a smaller refolded diameter. Such a balloon may have an exaggerated gradual gentle shoulder, wherein the change from the diameter of the balloon shaft adjacent to the balloon membrane (to which the balloon membrane is tethered) to the diameter of the fully expanded balloon takes place over a relatively long distance. Upon deflation, such a balloon, even if it is a high-pressure balloon, may preferably collapse with its edges re-wrapped snugly on the shaft without heaping up. Most preferably, such a balloon maintains the diameter of the collapsed balloon (which consists of the collapsed balloon membrane and tapered catheter shaft) smaller than the more proximal shaft of the catheter.

The balloon in preferably fabricated from polyethylene or nylon. In specific, nonlimiting examples, where the balloon is to be used in a delivery system for stent placement in coronary arteries, the dimensions of the balloon may be as follows. The balloon may preferably reach, in an inflated state, a diameter ranging from 2.0 to 5.0 millimeters, and more preferably from 2.5 to 4.5 millimeters, and an internal pressure of from 0 to 20 atmospheres, and more preferably from 4 to 20 atmospheres. Such a balloon may preferably have a rated burst pressure of from 12 to 20 atmospheres.

5.4. METHODS OF STENT PLACEMENT

The following is a general description of a method for stent placement in a vessel having an ostial lesion. Various modifications to this method may be required depending on the structure into which the stent is to be placed, and the needs of particular patients. The method may be used for the placement of single or multiple self-expanding or non-self-expanding stents. Although the method is exemplified using a shuttle stent delivery system and a forward break segment, methods using other methods of stent deployment, whereby an activated forward or posterior break segment is used to stably and accurately position the stent, are readily apparent to the skilled artisan.

First, the vessel or similar structure for stenting may be identified, and a path for the ostial shuttle stent delivery system may be established. In various embodiments, a guiding catheter and a guide wire may be inserted to provide the proper path. The remainder of this exemplary description relates to the use of such a guiding catheter and guide wire, but the invention is not to be limited to such embodiments.

The guiding catheter should have an internal diameter large enough to accommodate the ancillary means for expansion (e.g., a balloon catheter) and the ostial shuttle stent delivery system; for example, and not by way of limitation, where a stent is to be placed in an ostial lesion of a coronary artery, an 8, 9 or 10 French external diameter guiding catheter and a guide wire having a 0.014" or 0.018" diameter may be used.

Then, an ostial shuttle stent delivery system with at least one expandable stent mechanically or by other means attached onto the ostial deployment segment in contracted condition may be loaded, in retrograde fashion coaxially over the shaft of an ancillary means of expansion (e.g., a balloon catheter) outside the patient in either over-the-catheter or monorail manner.

Next, the assembly comprising the ostial shuttle stent delivery system and the ancillary means of expansion (e.g., a balloon catheter) may be inserted into the guiding catheter over the guide wire.

Where an embolic filter or filters are to be used, a filter, in a collapsed state, may be advanced out of the guiding catheter distal to the lesion(s) while the remainder of the shuttle is retained inside the guiding catheter by the application of traction on the proximal ends of the shuttle kept outside the patient. The filter may then be expanded by an intrinsic or ancillary mechanism (see supra).

In the specific embodiment where a stent is to be placed in an ostial lesion of a coronary artery, the guiding catheter, containing the ostial shuttle stent delivery system and the ancillary means of expansion, may be passed, over the guide wire, into a position of the aorta proximal to the ostium of the coronary artery to be stented (see FIG. 6).

Next, while the ostial shuttle stent delivery system is retained on the shaft of the ancillary means of expansion (e.g., a balloon catheter) inside the guiding catheter by application of traction on its proximal end kept outside the patient, the ancillary means of expansion (e.g., balloon) may be advanced, over the guide wire, and may be positioned over the ostial lesion. The ancillary means of expansion may then be expanded (e.g., the balloon may be inflated) to predilate the lesion prior to stent placement (see FIG. 7).

The ancillary means may then be contracted (e.g., the balloon may be deflated), and then advanced to a position distal to the ostial lesion, while the ostial shuttle stent delivery system remains stationary in the guiding catheter (see FIG. 8). Alternatively, the ancillary means may be retracted into the shuttle stent delivery system, or may be maintained in position.

Of note, in certain circumstances, pre-dilatation may not be necessary. In such circumstances, the means for expansion may be advanced distal to the ostial lesion.

The ostial shuttle stent delivery system may then be advanced into the target vessel over the shaft of the ancillary means of expansion (e.g., the balloon catheter) (see FIG. 9), and then the guiding catheter may be withdrawn into the parent conduit vessel, leaving the deployment segment of the shuttle stent delivery system in the target vessel. Where the stent is to be placed in an ostial lesion of a coronary artery, the guiding catheter is pulled back into the aorta (see FIG. 10).

Next, the ostial deployment segment may be positioned so that its distal, stent bearing end remains in the ostium of the target vessel, but its proximal, forward break segment-bearing end is in the parent conduit vessel from which the target vessel branches. For stent placement in an ostial lesion of a coronary artery, the ostial deployment segment may be positioned so that its distal portion remains in the coronary artery but its proximal end is in the aorta (see FIG. 11).

The forward break segment may then be activated (expanded), such that its transverse diameter is larger than the ostium.

The ostial shuttle stent delivery system may then be advanced until the forward break segment stops against the wall of the parent conduit vessel from which the target vessel branches (e.g., the wall of the aorta; see FIG. 13).

A stent, carried on the ostial deployment segment, may then be moved into the desired position within (and preferably extending over) the ostial lesion, while the position of the ancillary means of expansion (e.g., the balloon catheter) is maintained by application of traction on their proximal ends kept outside the patient. Radiopaque markers defining the location of the stent(s) may aid in stent positioning.

The ancillary means of expansion may be withdrawn into the ostial deployment segment. In certain specific embodiments of the invention, this withdrawal may be facilitated by alterable distal tips of the shuttle stent delivery system, for example, wherein the tip is constructed of a thermal memory alloy such as nitinol, and a weak electrical current may be used to create a wider aperture to facilitate withdrawal of the ancillary means of expansion.

Next, the ancillary means of expansion may be expanded (e.g., the balloon may be inflated; see FIG. 14) to deploy the stent. Note that the expanded forward break segment protects the newly deployed stent from damage or dislodgement by the guiding catheter.

Where a stent is a self-expanding stent, expansion of the deployment segment creates a structural change that releases the constrained stent; for example, central expansion may release the stent from peripherally located sleeves which overlap the edges of the stent. In specific, non-limiting embodiments of the invention, pharmaceutical substances may be released by expansion of the ostial deployment segment.

Following deployment, the forward break segment may be deactivated (and allowed to resume its unexpanded configuration), the ancillary means of expansion may be contracted (e.g., the balloons may be deflated), and the ostial shuttle stent delivery system, guiding catheter, ancillary means of expansion, and guide wire, may be withdrawn from the patient. Alternatively, the guide wire may be left in the target vessel and another means of ancillary expansion (e.g., a high-pressure balloon of larger expanded diameter) or another means of assessment of stent position and geometry (e.g. intravascular ultrasound catheter) may be advanced into the treatment site and used appropriately.

Various publications are cited herein, which are hereby incorporated by reference in their entireties.

What is claimed is:

1. A method for placing a stent in a first vessel, branching off of a parent conduit second vessel, said first vessel having an ostial lesion, in a patient in need of such treatment, comprising (i) passing an ostial stent delivery catheter having, at its distal end, an ostial deployment segment comprising (a) a break segment capable of reversible expansion; and (b) an independently expandable portion onto which a stent is mounted;

(ii) positioning the ostial deployment segment such that the break segment is located in the parent conduit second vessel;

(iii) activating the break segment such that it assumes an expanded configuration;

(iv) advancing the ostial stent delivery catheter until the activated break segment stops as it is pressed against the wall of the parent conduit second vessel, whereby the stent is positioned within the ostial lesion;

(v) deploying the stent within the lesion;

(vi) deactivating the break segment so that it is no longer in an expanded configuration; and (vii) withdrawing the ostial stent delivery catheter from the patient.

* * * * *